US010092229B2

(12) United States Patent
Taub et al.

(10) Patent No.: US 10,092,229 B2
(45) Date of Patent: Oct. 9, 2018

(54) CALIBRATION OF ANALYTE MEASUREMENT SYSTEM

(75) Inventors: Marc Barry Taub, Mountain View, CA (US); Wesley Scott Harper, Alameda, CA (US); Glenn Howard Berman, Alameda, CA (US); Jean Mei Huang, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 844 days.

(21) Appl. No.: 13/172,823

(22) Filed: Jun. 29, 2011

(65) Prior Publication Data

US 2012/0108931 A1 May 3, 2012

Related U.S. Application Data

(60) Provisional application No. 61/359,774, filed on Jun. 29, 2010.

(51) Int. Cl.
*A61B 5/00* (2006.01)
*A61B 5/1468* (2006.01)
*A61B 5/145* (2006.01)
*A61B 5/1495* (2006.01)

(52) U.S. Cl.
CPC .......... *A61B 5/1468* (2013.01); *A61B 5/1495* (2013.01); *A61B 5/14532* (2013.01); *A61B 2560/0252* (2013.01)

(58) Field of Classification Search
CPC ............ A61B 5/14532; A61B 5/14546; A61B 5/1486; A61B 5/1495; A61B 5/14865
USPC ................................................. 600/347, 365
See application file for complete search history.

(56) References Cited

U.S. PATENT DOCUMENTS

| 3,581,062 | A | 5/1971 | Aston |
|---|---|---|---|
| 3,926,760 | A | 12/1975 | Allen et al. |
| 3,949,388 | A | 4/1976 | Fuller |
| 3,960,497 | A | 6/1976 | Acord et al. |
| 3,978,856 | A | 9/1976 | Michel |
| 4,036,749 | A | 7/1977 | Anderson |
| 4,055,175 | A | 10/1977 | Clemens et al. |
| 4,129,128 | A | 12/1978 | McFarlane |
| 4,245,634 | A | 1/1981 | Albisser et al. |
| 4,327,725 | A | 5/1982 | Cortese et al. |
| 4,344,438 | A | 8/1982 | Schultz |
| 4,349,728 | A | 9/1982 | Phillips et al. |
| 4,373,527 | A | 2/1983 | Fischell |
| 4,392,849 | A | 7/1983 | Petre et al. |
| 4,425,920 | A | 1/1984 | Bourland et al. |

(Continued)

FOREIGN PATENT DOCUMENTS

| DE | 4401400 | 7/1995 |
|---|---|---|
| EP | 0098592 | 1/1984 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Patricia Mallari
*Assistant Examiner* — Karen Toth
(74) *Attorney, Agent, or Firm* — Jackson & Co., LLP

(57) ABSTRACT

A method of calibrating an analyte measurement system is provided.

28 Claims, 17 Drawing Sheets

(56) References Cited

U.S. PATENT DOCUMENTS

| | | |
|---|---|---|
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,199,428 A | 8/1993 | Obel et al. |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Nigel et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,720,295 A | 2/1998 | Greenhut et al. |
| 5,733,259 A | 3/1998 | Valcke et al. |
| 5,735,285 A | 4/1998 | Albert et al. |
| 5,741,211 A | 4/1998 | Renirie et al. |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,820,551 A | 10/1998 | Hill et al. |
| 5,822,715 A | 10/1998 | Worthington et al. |
| 5,891,047 A | 4/1999 | Lander et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |

(56) References Cited

U.S. PATENT DOCUMENTS

| | | |
|---|---|---|
| 6,122,351 A | 9/2000 | Schlueter, Jr. et al. |
| 6,128,526 A | 10/2000 | Stadler et al. |
| 6,134,461 A | 10/2000 | Say et al. |
| 6,115,628 A | 11/2000 | Stadler et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,405,066 B1 | 6/2002 | Essenpreis et al. |
| 6,413,393 B1 | 7/2002 | Van Antwerp et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,985 B2 | 5/2004 | Poore et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,010,345 B2 | 3/2006 | Hill et al. |

(56) References Cited

U.S. PATENT DOCUMENTS

| | | |
|---|---|---|
| 7,011,630 B2 | 3/2006 | Desai et al. |
| 7,016,713 B2 | 3/2006 | Gardner et al. |
| 7,016,720 B2 | 3/2006 | Kroll |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub et al. |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,826,981 B2 | 11/2010 | Goode, Jr. et al. |
| 7,857,760 B2 | 12/2010 | Brister et al. |
| 7,866,026 B1 | 1/2011 | Wang et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,914,450 B2 | 3/2011 | Goode, Jr. et al. |
| 7,938,797 B2 | 5/2011 | Estes |
| 7,946,984 B2 | 5/2011 | Brister et al. |
| 7,974,672 B2 | 7/2011 | Shults et al. |
| 8,060,173 B2 | 11/2011 | Goode, Jr. et al. |
| 8,116,837 B2 | 2/2012 | Huang |
| 8,140,312 B2 | 3/2012 | Hayter et al. |
| 8,160,900 B2 | 4/2012 | Taub et al. |
| 8,170,803 B2 | 5/2012 | Kamath et al. |
| 8,211,016 B2 | 7/2012 | Budiman |
| 8,216,137 B2 | 7/2012 | Budiman |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,282,549 B2 | 10/2012 | Brauker et al. |
| 8,376,945 B2 | 2/2013 | Hayter et al. |
| 8,444,560 B2 | 5/2013 | Hayter et al. |
| 8,457,703 B2 | 6/2013 | Al-Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,113,828 B2 | 8/2015 | Budiman |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,558,325 B2 | 1/2017 | Hayter et al. |
| 2001/0041831 A1 | 11/2001 | Starkweather et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0065454 A1 | 5/2002 | Lebel et al. |
| 2002/0068860 A1 | 6/2002 | Clark |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0161288 A1 | 10/2002 | Shin et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |

(56) References Cited

U.S. PATENT DOCUMENTS

| | | |
|---|---|---|
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1* | 7/2005 | Rasdal et al. ................ 600/347 |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0222566 A1 | 10/2006 | Brauker et al. |

(56) References Cited

U.S. PATENT DOCUMENTS

| | | |
|---|---|---|
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149873 A1 | 6/2007 | Say et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0282299 A1 | 12/2007 | Hellwig |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0179187 A1 | 7/2008 | Ouyang et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0314395 A1 | 8/2008 | Kovatchev et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278332 A1 | 11/2008 | Fennel et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0319279 A1 | 12/2008 | Ramsay et al. |
| 2008/0319295 A1 | 12/2008 | Bernstein et al. |

(56) References Cited

U.S. PATENT DOCUMENTS

| | | |
|---|---|---|
| 2008/0319296 A1 | 12/2008 | Bernstein et al. |
| 2009/0005665 A1* | 1/2009 | Hayter .............. A61B 5/14532 600/365 |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0054749 A1 | 2/2009 | He |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1* | 4/2009 | Talbot .................... G06Q 50/24 705/3 |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Ying et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0156919 A1 | 6/2009 | Brister et al. |
| 2009/0156924 A1* | 6/2009 | Shariati et al. .............. 600/365 |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0182517 A1* | 7/2009 | Gandhi ................ A61N 1/3708 702/58 |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0257911 A1 | 10/2009 | Thomas et al. |
| 2009/0281406 A1 | 11/2009 | McGarraugh et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081906 A1 | 4/2010 | Hayter et al. |
| 2010/0081909 A1* | 4/2010 | Budiman ............ A61B 5/14532 600/365 |
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0152561 A1 | 6/2010 | Goodnow et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0230285 A1 | 9/2010 | Hoss et al. |
| 2010/0234710 A1 | 9/2010 | Budiman et al. |
| 2010/0261987 A1 | 10/2010 | Kamath et al. |
| 2010/0265073 A1 | 10/2010 | Harper et al. |
| 2010/0274515 A1* | 10/2010 | Hoss .................. A61B 5/14532 702/104 |
| 2010/0277342 A1 | 11/2010 | Sicurello et al. |
| 2010/0280441 A1 | 11/2010 | Willinska et al. |
| 2010/0280782 A1 | 11/2010 | Harper et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0040163 A1 | 2/2011 | Telson et al. |

(56) References Cited

U.S. PATENT DOCUMENTS

| | | |
|---|---|---|
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0082484 A1 | 4/2011 | Saravia et al. |
| 2011/0105873 A1 | 5/2011 | Feldman et al. |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0184268 A1* | 7/2011 | Taub ............... A61B 5/14532 600/365 |
| 2011/0190603 A1 | 8/2011 | Stafford |
| 2011/0191044 A1 | 8/2011 | Stafford |
| 2011/0193704 A1 | 8/2011 | Harper et al. |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0224523 A1 | 9/2011 | Budiman |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0288574 A1 | 11/2011 | Curry et al. |
| 2011/0319729 A1 | 12/2011 | Donnay et al. |
| 2011/0320130 A1 | 12/2011 | Valdes et al. |
| 2011/0320167 A1 | 12/2011 | Budiman |
| 2012/0010642 A1 | 1/2012 | Lee et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0209099 A1 | 8/2012 | Ljuhs et al. |
| 2012/0215462 A1 | 8/2012 | Goode et al. |
| 2012/0245447 A1 | 9/2012 | Karan et al. |
| 2012/0277565 A1 | 11/2012 | Budiman |
| 2013/0035575 A1 | 2/2013 | Mayou et al. |
| 2013/0184547 A1 | 7/2013 | Taub et al. |
| 2013/0231541 A1 | 9/2013 | Hayter et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2014/0121480 A1 | 5/2014 | Budiman et al. |
| 2014/0121488 A1 | 5/2014 | Budiman |
| 2014/0221966 A1 | 8/2014 | Buckingham et al. |
| 2015/0216456 A1 | 8/2015 | Budiman |
| 2015/0241407 A1 | 8/2015 | Ou et al. |
| 2015/0366510 A1 | 12/2015 | Budiman |
| 2016/0022221 A1 | 1/2016 | Ou et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| JP | 2004-358261 | 12/2004 |
| WO | WO-1996/025089 | 8/1996 |
| WO | WO-1996/035370 | 11/1996 |
| WO | WO-1997/015227 | 5/1997 |
| WO | WO-1998/035053 | 8/1998 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/058537 | 8/2002 |
| WO | WO-2003/076893 | 9/2003 |
| WO | WO-2003/082091 | 10/2003 |
| WO | WO-2003/085372 | 10/2003 |
| WO | WO-2004/060455 | 7/2004 |
| WO | WO-2004/061420 | 7/2004 |
| WO | WO-2005/010756 | 2/2005 |
| WO | WO-2005/041766 | 5/2005 |
| WO | WO-2005/065542 | 7/2005 |
| WO | WO-2005/089103 | 9/2005 |
| WO | WO-2006/024671 | 3/2006 |
| WO | WO-2006/079114 | 7/2006 |
| WO | WO-2006/081336 | 8/2006 |
| WO | WO-2006/085087 | 8/2006 |
| WO | WO-2006/086423 | 8/2006 |
| WO | WO-2007/097754 | 8/2007 |
| WO | WO-2008/001366 | 1/2008 |
| WO | WO-2008/086541 | 7/2008 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

Blendea, M. C., et al, "Heart Disease in Diabetic Patients", *Current Diabetes Reports*, vol. 3, 2003, pp. 223-229.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Diabetes Control and Complications Trial Research Group, "The Effect of Intensive Treatment of Diabetes on the Development and Progression of Long-Term Complications in Insulin-Dependent Diabetes Mellitus," *New England J. Med.* vol. 329, 1993, pp. 977-986.

Eckert, B. et al. "Hypoglycaemia Leads to an Increased QT Interval in Normal Men," Clinical Physiology, vol. 18, No. 6, 1998, pp. 570-575.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Georgescu, B., et al., "Real-Time Multimodel Tracking of Myocardium in Echocardiography Using Robust Information Fusion", *Medical Image Computing and Computer-Assisted Intervention*, 2004, pp. 777-785.

Goldman, J. M., et al., "Masimo Signal Extraction Pulse Oximetry", *Journal of Clinical Monitoring and Computing*, vol. 16, No. 7, 2000, pp. 475-483.

Harris, N.D., et al., "Can Changes in QT Interval be Used to Predict the Onset of Hypoglycemia in Type 1 Diabetes?", *Computers in Cardiology*, vol. 27, 2000, pp. 375-378.

Heller, S. R., "Abnormalities of the Electrocardiogram During Hypoglycemia: The Cause of the Dead in Bed Syndrome?" *International Journal of Clinical Practice*, Suppl. No. 129, 2002, pp. 27-32.

Isermann, R., "Supervision, Fault-Detection and Fault-Diagnosis Methods—An Introduction", *Control Engineering Practice*, vol. 5, No. 5, 1997, pp. 639-652.

(56) References Cited

OTHER PUBLICATIONS

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jones, T. W., et al., "Mild Hypoglycemia and Impairment of Brain Stem and Cortical Evoked Potentials in Healthy Subjects," *Diabetes* vol. 39, 1990, 1550-1555.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Landstedt-Hallin, L., et al., "Increased QT Dispersion During Hypoglycaemia in Patients with Type 2 Diabetes Mellitus," Journal of Internal Medicine, vol. 246, 1999, 299-307.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Maher, "A Method for Extrapolation of Missing Digital Audio Data", *Preprints of Papers Presented at the AES Convention*, 1993, pp. 1-19.

Maher, "Audio Enhancement using Nonlinear Time-Frequency Filtering", *AES 26th International Conference*, 2005, pp. 1-9.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Malmberg, K., "Prospective Randomised Study of Intensive Insulin Treatment on Long-Term Survival After Acute Myocardial Infarction in Patients with Diabetes Mellitus", British Medical Journal, vol. 314, 1997, pp. 1512-1515.

Markel, A. et al, "Hypoglycaemia-Induced Ischaemic ECG Changes", Presse Medicale, vol. 23, No. 2, 1994, pp. 78-79.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Okin, P. M., et al, "Electrocardiographic Repolarization Complexity and Abnormality Predict All-Cause and Cardiovascular Mortality in Diabetes," *Diabetes*, vol. 53, 2004, pp. 434-440.

Peterson, K., et al., "Regulation of Serum Potassium During Insulin-Induced Hypoglycemia," *Diabetes*, vol. 31, 1982, pp. 615-617.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Rana, B. S., et al., "Relation of QT Interval Dispersion to the Number of Different Cardiac Abnormalities in Diabetes Mellitus", *The American Journal of Cardiology*, vol. 90, 2002, pp. 483-487.

Robinson, R. T. C. E., et al. "Changes in Cardiac Repolarization During Clinical Episodes of Nocturnal Hypoglycaemia in Adults with Type 1 Diabetes," *Diabetologia*, vol. 47, 2004, pp. 312-315.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Steinhaus, B. M., et al., "The Information Content of the Cardiac Electrogram at the Stimulus Site," *Annual International Conference of the IEEE Engineering in Medicine and Biology Society*, vol. 12, No. 2, 1990, 0607-0609.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Whipple, G., "Low Residual Noise Speech Enhancement Utilizing Time-Frequency", *Proceedings of the International Conference on Acoustics, Speech, and Signal Processing*, vol. 19, 1994, pp. I5-I8.

Wilson, G. S., et al., "Progress Toward the Development of an Implantable Sensor for Glucose", *Clinical Chemistry*, vol. 38, No. 9, 1992, pp. 1613-1617.

(56) References Cited

OTHER PUBLICATIONS

Wolfe, P. J., et al., "Interpolation of Missing Data Values for Audio Signal Restoration Using a Gabor Regression Model", *2005 IEEE International Conference on Acoustics, Speech, and Signal Processing*, vol. 5, 2005, pp. 517-520.

Alemzadeh, R, "Sensor-Augmented Insulin Pump Therapy: Clinical Applications", *Medical College of Wisconsin Diabetes Symposium*, pp. 1-61, 2011.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", *Biosensors and Bioelectronics*, vol. 17, No. 8, 2002, pp. 647-654.

Guerci, B., et al., "Clinical Performance of CGMS in Type 1 Diabetic Patients Treated by Continuous Subcutaneous Insulin Infusion Using Insulin Analogs", *Diabetes Care*, vol. 26, 2003, pp. 582-589.

Kovatchev, B. P., et al., "Evaluating the Accuracy of Continuous Glucose-Monitoring Sensors", *Diabetes Care*, vol. 27, No. 8, 2004, pp. 1922-1928.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.

Arnold, M. A., et al., "Selectivity Assessment of Noninvasive Glucose Measurements Based on Analysis of Multivariate Calibration Vectors", *Journal of Diabetes Science and Technology*, vol. 1, No. 4, 2007, pp. 454-462.

Eren-Oruklu, M., et al., "Estimation of Future Glucose Concentrations with Subject-Specific Recursive Linear Models", *Diabetes Technology & Therapeutics* vol. 11(4), 2009, pp. 243-253.

Boyne, M. S., et al., "Timing of Changes in Interstitial and Venous Blood Glucose Measured With a Continuous Subcutaneous Glucose Sensor", *Diabetes*, vol. 52, Nov. 2003, pp. 2790-2794.

Hovorka, R., et al., "Nonlinear Model Predictive Control of Glucose Concentration in Subjects with Type 1 Diabetes", *Physiological Measurement*, vol. 55, Jul. 2004, pp. 905-920.

Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.

Steil, G. M., et al., "Closed-Loop Insulin Delivery—the Path of Physiological Glucose Control", *Advanced Drug Delivery Reviews*, vol. 56, 2004, pp. 125-144.

Kovatchev, B. P., et al., "Graphical and Numerical Evaluation of Continuous Glucose Sensing Time Lag", Diabetes Technology & Therapeutics, vol. 11, No. 3, 2009, pp. 139-143.

Dassau, E., et al., "Detection of a Meal Using Continuous Glucose Monitoring", *Emerging Treatments and Technologies*, vol. 31, No. 2, Feb. 2008, pp. 295-300.

Hyunjin, L., et al., "A Closed-Loop Artificial Pancreas Using Model Predictive Control and a Sliding Meal Size Estimator", *Journal of Diabetes Science and Technology*, vol. 3, Issue 5, Sep. 2009, pp. 1082-1090.

\* cited by examiner

CALIBRATION OF ANALYTE MEASUREMENT SYSTEM

RELATED APPLICATION

The present application claims the benefit of U.S. Provisional Application No. 61/359,774 filed Jun. 29, 2010 entitled "Calibration of Analyte Measurement System," the disclosure of which is incorporated herein by reference for all purposes.

BACKGROUND

Monitoring of the level of glucose or other analytes, such as lactate or oxygen, in certain individuals is vitally important to their health. High or low levels of glucose or other analytes may have detrimental effects. Monitoring of glucose is particularly important to individuals with diabetes. Diabetics may need to monitor glucose levels to determine when insulin is needed to reduce glucose levels in their bodies or when additional glucose is needed to raise the level of glucose in their bodies. In non-diabetic individuals, it may be important to monitor glycemic responses to determine whether therapeutic approaches may be useful to prevent the onset of diabetes.

Analyte monitoring systems may be designed to test blood samples taken periodically and measured outside of the body (in vitro testing), such as by putting a drop of blood on a test strip, and performing an analyte analysis on the test strip. Blood may be taken from a finger (by performing a "fingerstick") or other locations on the body, such as the arm, thigh, etc. Tests performed in such a manner may be referred to as "discrete" measurements, and in the case of glucose measurements, "blood glucose" (BG) measurements. Other systems are designed to measure analyte levels within the body (in vivo), using a suitable sensor, without drawing blood for every measurement. Certain systems have combined functionality for performing both sensor-based as well as discrete measurements.

In some situations, it is medically desirable to monitor analyte levels in a subject closely, over a substantial period of time, or on an ongoing basis for an extended time period, in some cases indefinitely. A monitor that tracks glucose levels by automatically taking periodic in vivo measurements, e.g., one measurement per minute, or more or less frequently, is known as a "continuous glucose monitor" (CGM). Prior art CGMs have been provided, for example, in the form of a system. A portion of the system, comprising an electrochemical sensor partially inserted into the skin, and an associated processor and transmitter, with a self-contained power supply, is attached to the body of the user and will remain in place for an extended period of hours, days, weeks, etc. The transmitter takes analyte measurements periodically and transmits them, for example, by short-range radio communications, to a separate receiver/display device. The receiver/display device will typically receive discrete BG measurements (e.g., from a separate BG meter or an included BG test strip port), as well as a port, such as a USB port, for communications with upstream computers and/or other electronics. In some embodiments, the receiver unit may be directly or indirectly interfaced with an insulin pump, for managing the subject's insulin therapy.

The accuracy of the analyte measurements obtained with an in vivo sensing system is important. Calibration of such systems may be performed by comparing in vivo "system" measurements against discrete BG "reference" measurements from fingerstick samples measured on a test strip.

CGM systems typically perform calibrations on a fixed schedule. However, such a fixed schedule may impose inconvenience on the user if a required calibration occurs when a user is occupied with other activities or asleep. In some instances a required calibration may occur when analyte levels are in a state of instability or rapid change. Calibrations taken during such times of unstable analyte levels may sometimes provide less than optimal results. Accordingly, it would be desirable to provide calibration routines which allow customization by user. It would also be desirable to provide calibration routines which calibrate when the analyte levels and rates of change are more desirable for accurate measurement and observation.

SUMMARY

An analyte measurement system and a method for calibrating a signal from an electrochemical sensor are provided. A signal is generated from the sensor, which corresponds to an analyte concentration level in a biofluid of a subject. A user interface prompts a user to assay a calibration sample of the user's blood to obtain a calibration value if a first condition is met. A processor is configured to correlate the calibration value to at least one of the signals from the sensor if the first condition is met.

In some embodiments the method further includes selecting a first time frame. In some embodiments, the method includes selecting a maximum number of calibrations in the first time frame. The first condition may be met if fewer than the maximum number of calibrations has occurred in the first time frame.

In some embodiments the method further includes selecting a second time frame. The method may include selecting a maximum number of calibrations in the second time frame. The first condition may be met if fewer than the maximum number of calibrations has occurred in the second time frame.

In some embodiments, the method further includes prompting the user to assay a calibration sample of the user's blood to obtain a calibration value if a second condition is met. The method may further include allowing the user to select a time period in which calibrations are not accepted. The second condition may be met if the current time is outside the selected time period.

In some embodiments, the system further includes prompting the user to assay a calibration sample of the user's blood to obtain a calibration value, if a third condition is met. The method may include determining the existence of a condition relating the subject. In some embodiments, the condition comprises a determination of whether the subject is asleep. The third condition may be met if the condition does not exist. In some embodiments, the analyte is glucose.

In some embodiments, the assayed calibration sample is obtained from a finger stick testing site. In some embodiments, the assayed calibration sample is obtained from an alternative site test. The location of the assayed calibration sample may be the leg of a user, or the abdomen of a user. Obtaining the calibration measurement may include determining the calibration measurement in less than or equal to about 1 µL of blood. In some embodiments, the calibration value is compared to at least one signal from the sensor for use in calibrating the sensor.

An analyte measurement system and a method for calibrating a signal from an electrochemical sensor is provided, which includes generating a signal from the sensor, the signal corresponding to an analyte concentration level in a biofluid of a subject; providing a user the option to select a time for obtaining a calibration sample of the user's blood to obtain a calibration value; and correlating the calibration value to at least one of the signals from the sensor if the current time corresponds to the selected time.

In some embodiments, the method includes providing a user an option to select a time comprises providing a user the option to select a date and a time for calibration. The method may include providing a user an option to select a time comprises providing a user the option to select a time for recurrent daily calibration. In some embodiments, the analyte is glucose.

An analyte measurement system and a method for calibrating a signal from an electrochemical sensor is provided which includes generating a signal from the sensor, the signal corresponding to an analyte concentration level in a biofluid of a subject; determining whether calibration is accepted; and providing a user the option to obtain a calibration sample of the user's blood to obtain a calibration value if calibration is accepted; and correlating the calibration value to at least one of the signals from the sensor.

In some embodiments, the predetermined time is fifteen minutes. In some embodiments, calibration is accepted if the rate of change of the signal is within a predetermined threshold. The method may further include determining the likelihood of successful calibration. In some embodiments, an icon is provided in a display unit relating to the likelihood of successful calibration.

An analyte measurement system and a method for calibrating a signal from an electrochemical sensor is provided which includes generating a signal from the sensor, the signal corresponding to an analyte concentration level in a biofluid of a subject; determining a predetermined calibration time; determining a prospective calibration window running prior to the predetermined calibration time; and allowing calibration if a reference analyte measurement is available during the prospective calibration window.

In some embodiments, the method includes providing a grace period after the predetermined calibration time, and providing an alarm if no calibration is performed during the time period beginning with the predetermined calibration time and ending with the expiration of the grace period. In some embodiments, the alarm is suppressed if a reference analyte measurement is available during the prospective calibration window.

In some embodiments, the user is notified if a reference analyte measurement is being accepted for calibration.

In some embodiments, the prospective calibration window comprises a time period of 10 minutes, 30 minutes prior, or one hour prior to the predetermined calibration time.

An analyte measurement system and a method for calibrating a signal from an electrochemical sensor is provided which includes generating a signal from the sensor, the signal corresponding to an analyte concentration level in a biofluid of a subject; determining a condition relating to the stability of the sensor signal; and allowing calibration if the sensor stability is within a predetermined threshold.

In some embodiments, the predetermined threshold comprises a sensor stability of about 1 mg/dL/min. In some embodiments, the method further includes determining the duration of sensor operation and determining stability of the sensor signal at a reference duration of sensor operation. A calibration may be requested if the stability of the sensor signal at the reference duration of sensor operation is below a threshold. The reference duration of sensor operation may refer to an elapsed time following insertion of the sensor in the subject. In some embodiments, the reference duration comprises four hours.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part. Like reference numerals used in different figures denote like components or process steps. Reference numerals that differ only in the hundreds or thousands place from reference numerals in earlier figures refer (unless the context requires otherwise) to components or process steps that may be adapted from the corresponding component or process step in the prior Figure.

DETAILED DESCRIPTION

Figure 1:
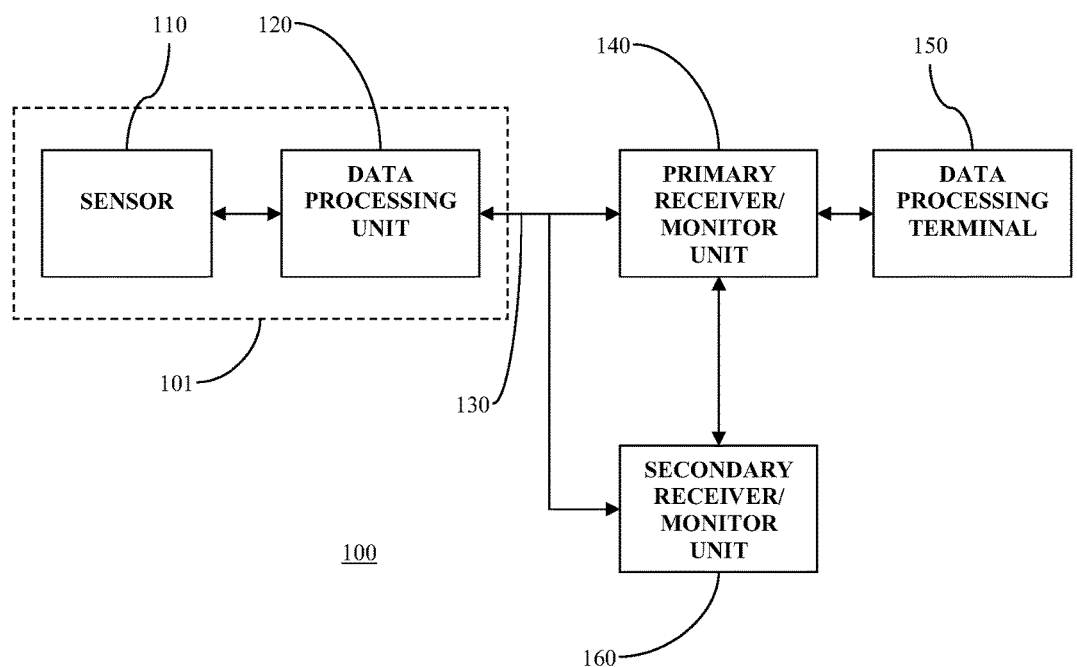
FIG. 1 is a block diagram of the components of an analyte monitoring system in accordance with one embodiment of the present disclosure.

A detailed description of the disclosure is provided herein. It should be understood, in connection with the following description, that the subject matter is not limited to particular embodiments described, as the particular embodiments of the subject matter may of course vary. It is also to be understood that the terminology used herein is for the purpose of describing particular embodiments only, and is not intended to be limiting, since the scope of the disclosed subject matter will be limited only by the appended claims.

Where a range of values is provided, it is understood that each intervening value between the upper and lower limit of that range and any other stated or intervening value in that stated range, is encompassed within the disclosed subject matter. Every range stated is also intended to specifically disclose each and every "sub range" of the stated range. That is, each and every range smaller than the outside range specified by the outside upper and outside lower limits given for a range, whose upper and lower limits are within the range from said outside lower limit to said outside upper limit (unless the context clearly dictates otherwise), is also to be understood as encompassed within the disclosed subject matter, subject to any specifically excluded range or limit within the stated range. Where a range is stated by specifying one or both of an upper and lower limit, ranges excluding either or both of those stated limits, or including one or both of them, are also encompassed within the disclosed subject matter, regardless of whether or not words such as "from", "to", "through", or "including" are or are not used in describing the range.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated herein by reference for all purposes, including without limitation to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior invention. Further, the dates of publication provided may be different from the actual publication dates, which may need to be independently confirmed.

As used herein and in the appended claims, the singular forms "a", "an", and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order which is logically possible. Reference to a singular item, includes the possibility that there are plural of the same item present. When two or more items (for example, elements or processes) are referenced by an alternative "or", this indicates that either could be present separately or any combination of them could be present together except where the presence of one necessarily excludes the other or others.

Certain classes of analyte monitors are provided in small, lightweight, battery-powered and electronically-controlled systems. Such a system may be configured to detect signals indicative of in vivo analyte levels using an electrochemical sensor, and to process and/or collect such signals. In some embodiments, the portion of the system that performs this initial processing may be configured to transmit the initially processed data to another unit for further collection and/or processing. Such transmission may be effected, for example, via a wired connection, such as electrical contacts or a cable, or via a wireless connection, such as an IR or RF connection.

Certain analyte monitoring systems for in vivo measurement employ a sensor that measures analyte levels in interstitial fluids under the surface of the subject's skin. In certain embodiments, a sensor may be inserted transcutaneously or subcutaneously (i.e., at least partially through the skin), or, in other embodiments, may be inserted entirely or wholly implanted below the skin. A sensor in such a system may operate as an electrochemical cell. Such a sensor may use any of a variety of electrode configurations, such as a three-electrode configuration (e.g., with "working", "reference" and "counter" electrodes), driven by a controlled potential (potentiostat) analog circuit, a two-electrode system configuration (e.g., with only working and counter electrodes), which may be self-biasing and/or self-powered, and/or other configurations.

In certain systems, the analyte sensor is in communication with a data processing/transmitter unit; the term "transmitter unit" or "transmitter device" as used in this disclosure sometimes refers to such a combination of an analyte sensor with such a data processing/transmitter unit. Certain embodiments are modular. The transmitter device may be separately provided as a physically distinct assembly, and configured to transmit the analyte levels detected by the sensor over a communication link to a receiver/monitor unit, referred to in this disclosure as a "receiver unit" or "receiver device", or in some contexts, depending on the usage, as a "display unit," "handheld unit," or "meter".

The receiver unit may perform data analysis, etc. on the received analyte data to generate information pertaining to the monitored analyte levels. The receiver unit may incorporate a display screen, which can be used, for example, to display measured analyte levels. It is also useful for a user of an analyte monitor to be able to see trend indications (including the magnitude and direction of any ongoing trend), and such data may be displayed as well, either numerically, or by a visual indicator, such as an arrow that may vary in visual attributes, such as size, shape, color, animation, or direction. The receiver device may further incorporate a test strip port and related electronics in order to be able to make discrete (e.g., BG) measurements.

The modularity of these systems may vary. In some embodiments the sensor is attachable and detachable from the transmitter (and transmitter reusable), while in other embodiments, the sensor and transmitter may be provided as an integrated package, which may be disposable.

To provide flexibility in analyte sensor manufacturing and/or design, it may be desirable for the transmitter device to accommodate a substantial range of analyte sensor sensitivities. Methods and systems for measuring sensor sensitivity are desirable in such cases, so that the analyte monitor may be accurately calibrated.

FIG. 1 shows one embodiment of an analyte measurement system 100. In such a system, a data processing unit or sensor control unit 120 may interact with an analyte sensor 110 to obtain signals representative of analyte levels. Data processing unit 120 may further include a communications circuit with associated electronics (not shown). In some embodiments, the data processing unit 120 and sensor 110 are disposed on the body of the subject. Accordingly, the data processing unit 120 and the sensor 110 may be referred to collectively herein as an "on-body unit" 101. A receiver unit or monitor unit 140 may also be provided. In the embodiment shown, data processing unit 120 and receiver unit 140 communicate via connection 130 (which in certain embodiments may be a wireless RF connection). In some embodiments, a secondary receiver unit 160 may be provided. A data processing terminal 150 may provide further processing or review of analyte data.

In certain embodiments, system 100 may be a continuous glucose monitoring (CGM) system, and accordingly operate in a mode in which the communications via connection 130 have sufficient range to support a flow of data from on-body unit 101 to monitor unit 140. In some embodiments, the data flow in a CGM system is automatically provided by the on-body unit 101 to the monitor unit 140. For example, no user intervention may be required for the on-body unit 101 to send the data to the monitor unit 140. In some embodiments, the on-body unit 101 provides the signal relating to analyte level to the monitor unit 140 on a periodic basis. For example, the signal may be provided, e.g., automatically sent, on a fixed schedule, e.g., once every 250 ms, once a second, once a minute, etc. In some embodiments, the signal is provided to the monitor unit 140 upon the occurrence of an event, e.g., a hyperglycemic event or a hypoglycemic event, etc. In some embodiments, data processing unit 120 may further include local memory in which it may record "logged data" or buffered data collected over a period of time and provide the some or all of the accumulated data to monitor unit 140 periodically. In other embodiments, a separate data logging unit may be provided to acquire periodically transmitted data from data processing unit 120. Data transmission in a CGM system may be one-way communication, e.g., the on-body unit 101 provides data to the monitor unit 140 without receiving signals from the monitor unit 140. In some embodiments, two-way communication is provided between the on-body unit 101 and the monitor unit 140.

In some embodiments, a signal is provided to the monitor unit 140 "on demand." According to such embodiments, the monitor unit 140 requests a signal from the on-body unit 101, or the on-body unit 101 may be activated to send signal upon activation to do so. Accordingly, one or both of the on-body unit 101 and monitor unit 140 may include a switch activatable by a user or activated upon some other action or event, the activation of which causes analyte-related signals to be transferred from the on-body unit 101 to the monitor unit 140. For example, the monitor unit 140 is placed in close proximity with a transmitter device and initiates a data transfer, either over a wired connection, or wirelessly by various means, including, for example, various RF-carried encodings and protocols, such as radio frequency identification (RFID) protocols, and IR links.

In some embodiments, the signal relating to analyte level is instantaneously generated by the analyte sensor 110 upon receipt of the request, and transmitted to the monitor unit 140 as requested, and/or the signal relating to analyte level is periodically obtained, e.g., once every 250 ms, once a second, once a minute, etc. Upon receipt of the "on demand" request at the on-body unit 101, an analyte signal is provided to the monitor unit. In some cases, the signal provided to the monitor unit 140 includes the most recent analyte signal(s).

In further embodiments, additional data is provided to the monitor unit 140 "on demand." For example, analyte trend data may be provided. Such trend data may include two or more analyte data points to indicate that analyte levels are rising, falling, or stable. Analyte trend data may include data from longer periods of time, such as, e.g., several minutes, several hours, several days, or several weeks.

Further details regarding CGM and on demand systems are disclosed in, for example, U.S. Pat. No. 7,620,438, U.S. Patent Publication Nos. 2009/0054749 A1, published Feb. 26, 2009; 2007/0149873 A1, published Jun. 28, 2007; 2008/0064937 A1, published Mar. 13, 2008; 2008/0071157 A1, published Mar. 20, 2008; 2008/0071158 A1, published Mar. 20, 2008; 2009/0281406 A1, published Nov. 12, 2009; 2008/0058625 A1, published Mar. 6, 2008, now U.S. Pat. No. 7,920,907; 2009/0294277 A1, published Dec. 3, 2009; 2008/0319295 A1, published Dec. 25, 2008, now U.S. Pat. No. 8,597,188; 2008/0319296 A1, published Dec. 25, 2008, now U.S. Pat. No. 8,617,069; 2009/0257911 A1, published Oct. 15, 2009, now U.S. Pat. No. 8,252,229; 2008/0179187 A1, published Jul. 31, 2008; 2007/0149875 A1, published Jun. 28, 2007, now U.S. Pat. No. 8,515,518; 2009/0018425 A1, published Jan. 15, 2009, now U.S. Pat. No. 8,160,670; and pending U.S. patent application Ser. No. 12/625,524, filed Nov. 24, 2009, now U.S. Pat. No. 8,390,455; Ser. No. 12/625,525, filed Nov. 24, 2009 now U.S. Pat. No. 8,358,210; Ser. No. 12/625,528, filed Nov. 24, 2009, now U.S. Pat. No. 8,115,635; Ser. No. 12/628,201, filed Nov. 30, 2009; Ser. No. 12/628,177, filed Nov. 30, 2009; Ser. No. 12/628,198, filed Nov. 30, 2009; Ser. No. 12/628,203, filed Nov. 30, 2009; Ser. No. 12/628,210, filed Nov. 30, 2009; Ser. No. 12/393,921, filed Feb. 26, 2009; Ser. No. 12/698,124, filed Feb. 1, 2010; Ser. No. 12/495,709, filed Jun. 30, 2009; Ser. No. 12/714,439, filed Feb. 26, 2010; Ser. No. 12/842,013, filed Jul. 22, 2010; 61/163,006, filed Mar. 23, 2009; Ser. No. 12/495,730, filed Jun. 30, 2009; Ser. No. 12/495,712, filed Jun. 30, 2009, now U.S. Pat. No. 8,437,827; Ser. No. 12/807,278, filed Aug. 31, 2010; Ser. No. 12/873,301, filed Aug. 31, 2010; Ser. No. 12/870,818, filed Aug. 28, 2010; Ser. No. 12/873,302, filed Aug. 31, 2010; 61/249,535, filed Oct. 7, 2009; Ser. No. 12/544,061, filed Aug. 19, 2009; Ser. No. 12/625,185, filed Nov. 24, 2009, now U.S. Pat. No. 8,354,013; Ser. No. 12/625,208, filed Nov. 24, 2009; Ser. No. 12/624,767, filed Nov. 24, 2009; Ser. No. 12/242,780, filed Sep. 30, 2008; Ser. No. 12/183,602, filed Jul. 31, 2008; Ser. No. 12/211,014, filed Sep. 15, 2008, now U.S. Pat. No. 8,636,884; and Ser. No. 12/114,359, filed May 2, 2008, now U.S. Pat. No. 8,080,385, each of which is incorporated by reference in its entirety herein for all purposes.

Figure 2:
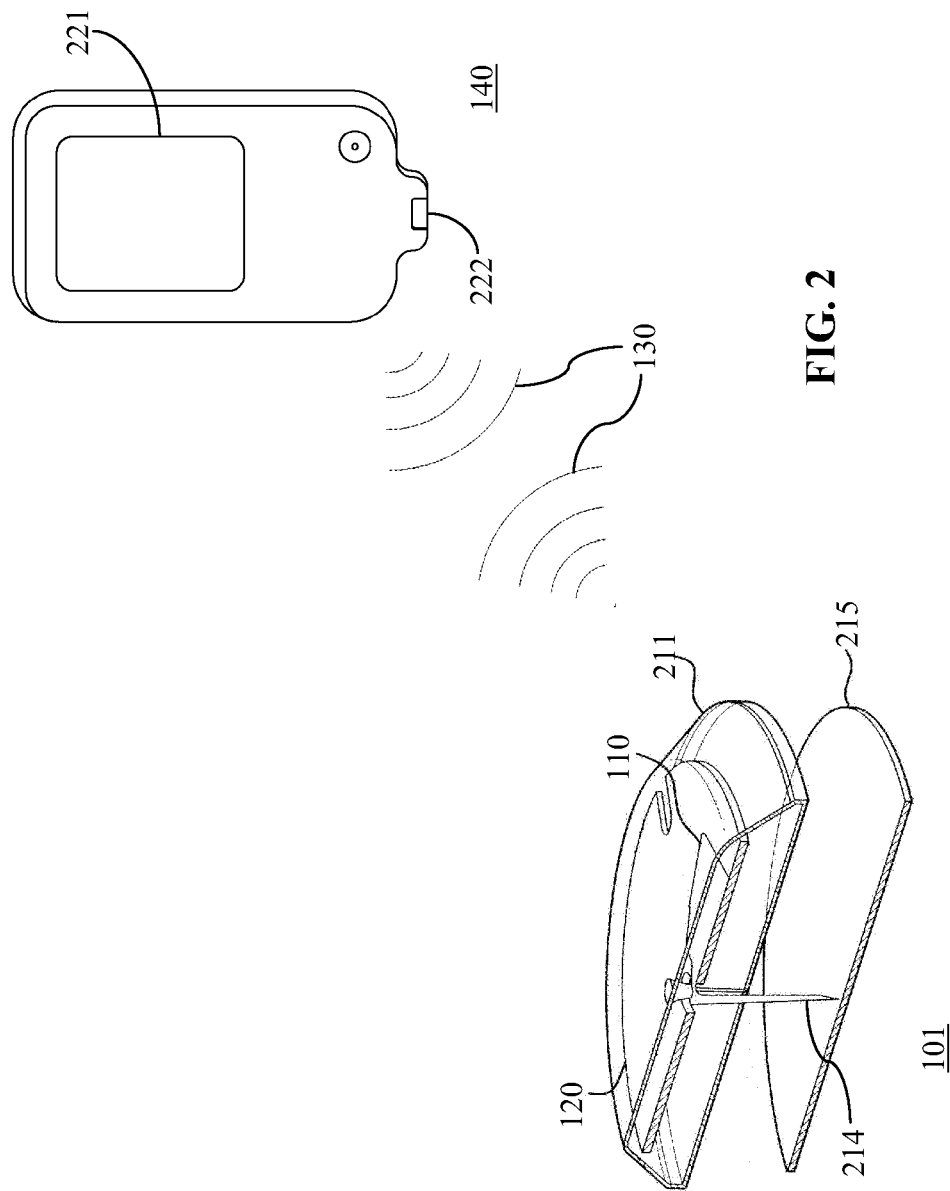
FIG. 2 is a schematic illustration of the components of an analyte monitoring system in accordance with one embodiment of the present disclosure.

An exemplary configuration for sensor 110 and data processing unit 120 (e.g., collectively on-body unit 101) is illustrated in FIG. 2. On-body unit 101, may be provided with a substantially circular configuration having a reduced height (i.e., "Z"-dimension) to provide a low-profile when sitting on the skin of the subject. Further, an adhesive patch 215 may be used to adhere the on-body unit 101 to the skin of the subject. On-body unit 101, including its associated electronics, are housing in sensor housing 211. For example, electronics may include, e.g., an analog interface for connecting to the sensor 110, a processor, and a power supply. A serial communication section may be provided. A temperature sensor, such as a thermistor detects skin and/or ambient temperature for determining temperature compensation to the analyte signal. An RF transmitter/receiver is provided to communicate with the receiver unit 140. A data storage unit, such as a memory, may be provided for storage of analyte data points over a short term, e.g., several hours or minutes, or over a long term, e.g., several days or weeks. Additional optional electronics include a serial communication section, a leakage detection circuit, or user input, e.g., a switch to activate/deactivate the device. Many of the enumerated components may be combined together and/or their function provided by common components. Furthermore, certain components may be eliminated entirely. For example, a power supply may be omitted if power is provided by inductive coupling.

In some embodiments, sensor 110 is disposed within the on-body unit 101, in a bent configuration. The contact portion of sensor 110 is oriented in a substantially horizontal configuration, and secured to a circuit board of on-body unit 101. The insertion portion 214 of the sensor 110 extends in a downwardly vertical orientation for placement in the skin of the subject. It is understood that sensor 110 may be disposed in other configurations, e.g., in an entirely substantially vertical configuration. As a further example, the insertion portion 214 may be disposed at an oblique angle, e.g., between 0° and 90° with respect to the skin surface.

As illustrated in FIG. 2, the on-body unit 101 communicates with the receiver unit 140 via communication link, which, as described above, may be a wireless communication link such as an RF or RFID communication link. Such communication may be one-way communication, e.g., from the on-body unit 101 to the receiver unit 140. In some embodiments, the communication may be two-way, e.g., both from the on-body unit 101 to the receiver unit 140 and from the receiver unit 140 to the on-body unit 101. In such cases, the receiving unit 140 may also be referred to herein as a display unit, transceiver or handheld unit. Communication between the on-body unit 101 and receiver unit 140 may occur via RF communication, inductive coupling, direct wired connection, etc.

The receiver unit 140 may perform data analysis, etc., on the received analyte data to generate information pertaining to the monitored analyte levels. The receiver unit may incorporate a display screen 221, which can be used, for example, to display measured analyte levels. It is also useful for a user of an analyte monitor to be able to see trend indications (including the magnitude and direction of any ongoing trend), and such data may be displayed as well, either numerically, or by a visual indicator, such as an arrow that may vary in visual attributes, such as size, shape, color, animation, or direction. The receiver device may further incorporate a test strip port 222 and related electronics in order to be able to make discrete (e.g., BG) measurements.

The modularity of these systems may vary. In some embodiments the sensor is attachable and detachable from the transmitter (and transmitter reusable), while in other embodiments, the sensor and transmitter may be provided as an integrated package, which may be disposable.

To provide flexibility in analyte sensor manufacturing and/or design, it may be desirable for the transmitter device to accommodate a substantial range of analyte sensor sensitivities. Methods and systems for measuring sensor sensitivity are desirable in such cases, so that the analyte monitor may be accurately calibrated. In the present invention, novel methods for measuring sensor sensitivity are provided, as described below.

The sensor 110 of the analyte measurement system 100 may be used to monitor levels of a wide variety of analytes. Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

In one embodiment of the present disclosure, sensor 110 is physically positioned in or on the body of a user whose analyte level is being monitored. Sensor 110 may be configured to continuously sample the analyte level of the user and convert the sampled analyte level into a corresponding data signal for analysis and/or transmission by data processing unit 120. Alternatively, sensor 110 may be configured to provide analyte levels on demand, e.g., upon request, from a separate device.

The sensor 110 may take on a number of forms. For example, the sensor 110 may include a flexible or rigid substrate. In some embodiments, the sensor 110 may be a wire. In some embodiments, the sensor 110 may include two or three or more electrodes.

In some embodiments, sensor 110 includes a substrate which is a dielectric, e.g., a polymer or plastic material, such as polyester or polyamide. In certain embodiments, the sensor 110 is constructed so that a portion is positionable beneath skin and a portion is above skin. Accordingly, sensor 110 includes an insertion portion and a contact portion. The contact portion typically includes several conductive contacts for connection to other electronics, e.g., at the data processing unit 120. In certain embodiments, the contacts provided are for a working electrode, a reference electrode, and a counter electrode. In some embodiments, two or more working electrodes are provided. The operative portions of these electrodes, that is, the working electrode, reference electrode, and counter electrode, are provided at the distal end of insertion portion of sensor 110. The contact and operative portions of the electrodes are connected by circuit traces running on the surface of the substrate. In some embodiments, the traces are provided in channels, or may be embedded within the substrate, or may traverse different sides of the substrate. The conductive contacts, conductive traces, and electrodes are fabricated from a conductive material, such as platinum, palladium, gold, or conductive carbon. Further details of sensors are described, e.g., in U.S. Pat. Nos. 6,175,572, 6,103,033, and 6,134,461, the disclosures of each of which are incorporated by reference herein.

In use, the sensor 110 may be configured to bend and therefore be positioned in two substantially perpendicular, intersecting planes.

In general, sensors in accordance with the present disclosure operate electrochemically, through an arrangement of electrodes having chemical sensing layers applied thereto, by generating an electrical current proportional to the volume of a redox reaction of the analyte (and indicative of analyte concentration), catalyzed by an analyte-specific oxidizing enzyme. Embodiments exist in which the number of electrodes provided to bring about and detect the level of these reactions is two, three or a greater number.

A portion of sensor 110 may be situated above the surface of the skin, with a distal portion 214 penetrating through the skin and into the subcutaneous space in contact with the user's biofluid, such as interstitial fluid. The disposition of the sensor in the illustrated embodiment is referred to as "transcutaneous" or "subcutaneous". In general, the terms "transcutaneous" and "subcutaneous" as used herein refer to a sensor that is only partially inserted under one or more layers of the skin of the user. In certain embodiments, sensor 110 is completely inserted under one or more layers of the skin of the user, i.e., wholly implanted beneath the skin surface. It is understood that many features described herein would be applicable to transcutaneous and subcutaneous sensors as well as wholly implanted sensors. Further details regarding the electrochemistry of sensor 110 is provided in, for example, U.S. Pat. Nos. 5,264,104; 5,356,786; 5,262,035; 5,320,725; 5,593,852; and 6,990,366, the disclosures of each of which are incorporated herein by reference for all purposes.

In some embodiments, the sensor is implantable into a subject's body for a period of time (e.g., three to seven days, or in some embodiments, longer periods of up to several weeks) to contact and monitor an analyte present in a biological fluid. In this regard, the sensor can be disposed in a subject at a variety of sites (e.g., abdomen, upper arm, thigh, etc.), including intramuscularly, transcutaneously, intravascularly, or in a body cavity.

In some embodiments, sensor 110 is employed by insertion and/or implantation into a user's body for some usage period. In such embodiments, the substrate may be formed from a relatively flexible material to improve comfort for the user and reduce damage to the surrounding tissue of the insertion site, e.g., by reducing relative movement of the sensor with respect to the surrounding tissue.

Certain embodiments of sensor 110 include three electrodes, while other embodiments can include a fewer or greater number of electrodes. For example, a two electrode sensor can be utilized. The sensor may be externally-powered and allow a current to pass proportional to the amount of analyte present. Alternatively, the sensor itself may act as a current source in some embodiments. In some two-electrode embodiments, the sensor may be self-biasing and there may be no need for a reference electrode. An exemplary self-powered, two-electrode sensor is described in U.S. patent application Ser. No. 12/393,921, filed Feb. 26, 2009, and entitled "Self-Powered Analyte Sensor," which is hereby incorporated by reference in its entirety herein for all purposes. The level of current provided by a self-powered sensor may be low, for example, on the order of nanoamperes.

Figure 3:
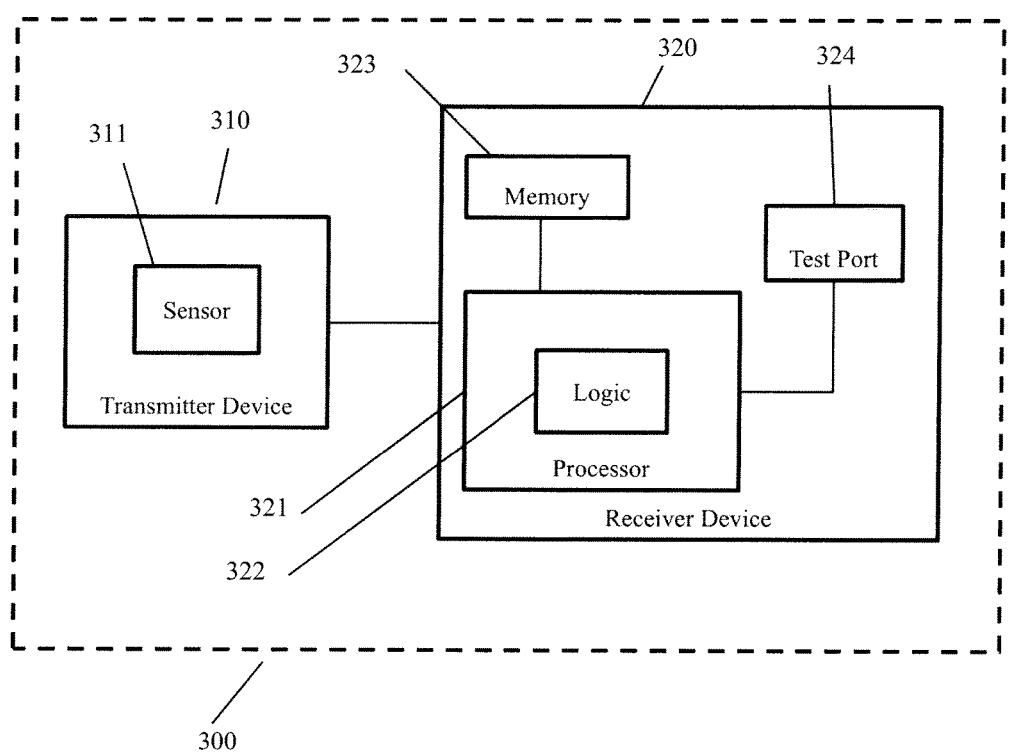
FIG. 3 is a block diagram of an on-demand analyte monitoring system in accordance with one embodiment of the present disclosure.

FIG. 3 illustrates an exemplary on-demand analyte monitoring system. System 300 may include analyte sensor 311 within transmitter device 310, at least one processor 321, logic 322 and optionally memory 323. In a system employing a remote receiver unit, such as receiver unit 320, in which the receiver unit 320 is performing the calibration of the transmitter device 310, or of the sensor element 311 in the transmitter device 310, processor 321 and memory 323 would be within and accessible to receiver unit 320.

The logic 322 portion of processor 321 can be implemented in several different ways. Processor 321 could comprise a general purpose computer, such as an embedded microprocessor, which could operate by executing machine-readable routines stored in memory 323. In such a case, logic 322 comprises the general purpose processing elements of processor 321, programmed to perform specific functions by the programming read from memory 323. Memory 323 could comprise read-only memory or firmware, or volatile memory loaded from a storage device (not shown), either at system startup (boot) or during run time. Alternatively, logic 322 could comprise a system of logic elements interconnected to perform the specified operations. Such a system could be provided in the form of discrete hard-wired logic, gate arrays, programmable gate arrays, and might include one or more Field Programmable Gate Arrays (FPGAs) or Application-Specific Integrated Circuits (ASICs).

For a more detailed discussion of continuous analyte monitoring devices, see, e.g., U.S. patent application Ser. No. 12/873,298, filed Aug. 31, 2010, hereby incorporated by reference herein in its entirety, for all purposes. Additional commonly assigned applications describe systems which comprise an "on-demand" analyte monitor, e.g., in which analyte measurements are either transmitted from the sensor/transmitter to the receiver unit or obtained from the sensor upon request of the user. See, e.g., U.S. patent application Ser. No. 13/011,898 filed Jan. 22, 2011 and U.S. patent application Ser. No. 12/807,278 filed Aug. 31, 2010, the disclosures of each of which are hereby incorporated by reference in their entirety herein for all purposes.

System 300 may also comprise an operative component configured to provide a reference analyte measurement. Such a component may be an analyte meter. The analyte meter may be a glucose meter comprising a test strip port. As shown in FIG. 3, receiver unit 320 incorporates test strip reader 324 for performing discrete in vitro analyte measurements, such as blood glucose (BG) measurements. In some embodiments, receiver unit 320 may also function as an analyte meter, e.g., a glucose meter. In other embodiments, receiver unit 320 may have a data entry provision, whereby a reading from a separate analyte monitor or meter may be input as reference test data.

In some embodiments, processor 321 includes logic 322 to perform the following functions: accept a reference analyte measurement of the subject, made other than with said sensor, perform, in response to a command from the user of the system, at least one test measurement of a level of analyte in the subject, and if the test measurement is performed within about a specified period before or after said noted time of said reference measurement, determine a calibration adjustment for use with said system, as a function of the reference measurement and the test measurement.

The logic 322 provided by processor 321 may cause a prompt to be provided to the user to perform a reference analyte measurement, such as a BG measurement from a finger stick. Such a prompt could be provided based on a calibration schedule established in system 300. The logic causes the system to accept the reference test if it satisfies specified criteria, as described above. If the reference test satisfies the specified criteria, the logic might further provide another prompt to be provided to the user, to perform a test analyte measurement using system 300. The logic might further provide the capability, through a suitable setup routine or otherwise, for the user to enable or disable issuance of an explicit prompt to perform the system measurement.

In some embodiments, the system requires the user to perform calibrations on a fixed schedule. For example, several calibrations may be scheduled on the first day of sensor wear, e.g., the first twenty-four hours following implantation of the sensor. Calibrations are typically required to address peculiarities of wearing a sensor under the skin on the first day. Without limiting the current disclosure, such peculiarities may be due to several mechanisms, such as the healing characteristics of the subject's body, the sensor chemistry, etc. In some embodiments, a pre-set calibration schedule is typically established at the factory and includes several times in which a calibration request is sent to a user. A user is typically unable to alter such calibration schedule. Such calibration schedule may be referred to herein as a "pre-set calibration schedule."

Proper calibration of a glucose monitor with a reference glucose reading is vital for accurate performance in certain embodiments. Calibration is the process where the conversion factor for the calculation of glucose from sensor data is determined, where the conversion factor (or sensitivity) is a ratio of the electrical current generated by the analyte sensor to the reference glucose value associated in line with this current signal.

To perform calibration based on discrete measurements, analyte monitoring system 100 may employ a substantial plurality of signal processing algorithms, which may be performed by a processor within data processing unit 120 and/or a processor in receiver unit 140, or a combination of those processors. Over the usable life of sensor 110, calibrations may be performed at various intervals in order to determine that the sensor is ready for use and continues to operate in a useful range, and to determine the sensitivity of the sensor so that accurate analyte concentration measurements may be provided.

Relevant functions that may be provided with regard to calibration may fall into two areas: (1) logic for scheduling calibrations, and (2) logic for performing calibrations.

Figure 4:
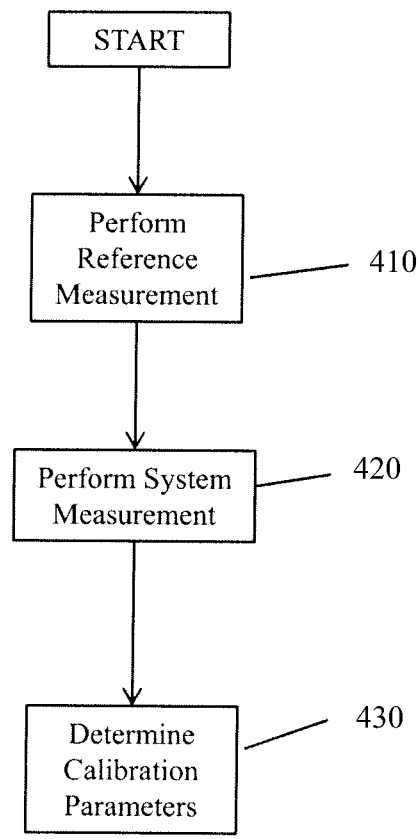
FIG. 4 is a flowchart showing, at a high level, the flow of calibration processing in certain embodiments.

FIG. 4 shows procedures for calibrating system 100. In general, such a procedure may comprise taking a discrete analyte measurement from the subject ("reference measurement" 410), taking at a proximate time an analyte measurement from the subject with system 100 ("system measurement" 420), and determining, based on such measurements, appropriate calibration parameters or sensitivity factor (S) for converting system measurements into concentration units (430).

The reference measurement may be a BG finger stick (in the case of the analyte being glucose), but also may be any measurement of analyte in the subject, blood-based or otherwise, taken by any means other than the system being calibrated.

Figure 5:
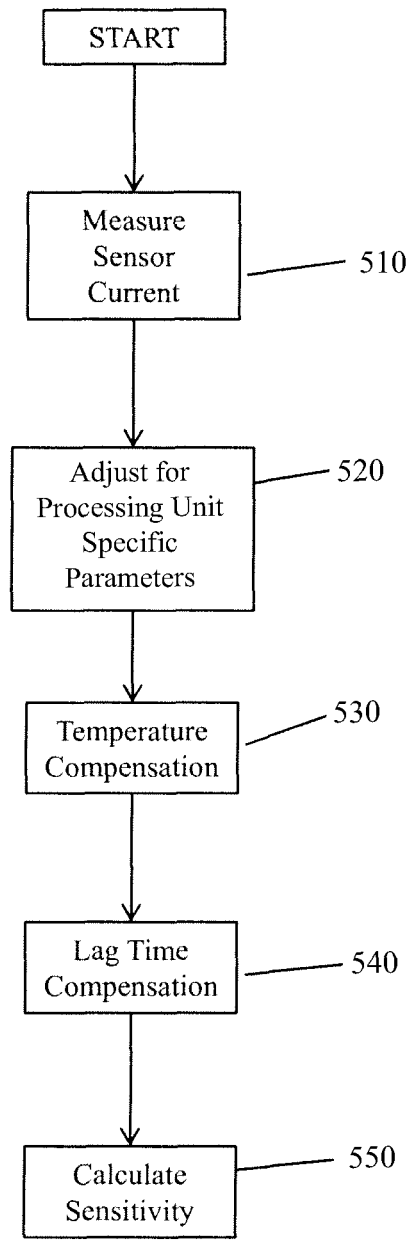
FIG. 5 is a flowchart further showing, at a high level, the flow of calibration processing in certain embodiments.

The procedure for taking a system measurement is further outlined in FIG. 5. The procedure may generally comprise a measurement taken from sensor 110 (510), which is processed by processor in data processing unit 120 or receiver 140. In some embodiments, the measurement from sensor 110 will be an electrical current.

Data processing or transmitter units may vary from one to another in terms of electrical and physical characteristics. Accordingly, the sensor current measurement may be adjusted for variations among processing units in accordance with parameters that characterize the particular data processing unit in use (520). The current may then be further subjected to temperature compensation (530) and, if sufficient data is available, lag time compensation (540), the latter being applied due to the delay in interstitial analyte concentration measurements as compared to discrete blood measurements, when the analyte level is changing.

An "immediate, real-time" sensitivity factor may be calculated (550) by dividing the temperature and lag-corrected sensor current by the reference measurement (each determined at appropriate times). Furthermore, a composite sensitivity may be calculated based on successive measurements, for example, two successive measurements, by performing a weighted average of the sensitivities calculated from the two measurements.

Note, however, that in order to proceed with any of the processing described above, it is also desirable to perform a plurality of tests (in some embodiments, a substantial plurality of tests), to ensure that the data utilized in the sensitivity determination (550) is valid. These validation checks will be described in connection with the more detailed discussion of calibration procedures that follows.

Figure 6:
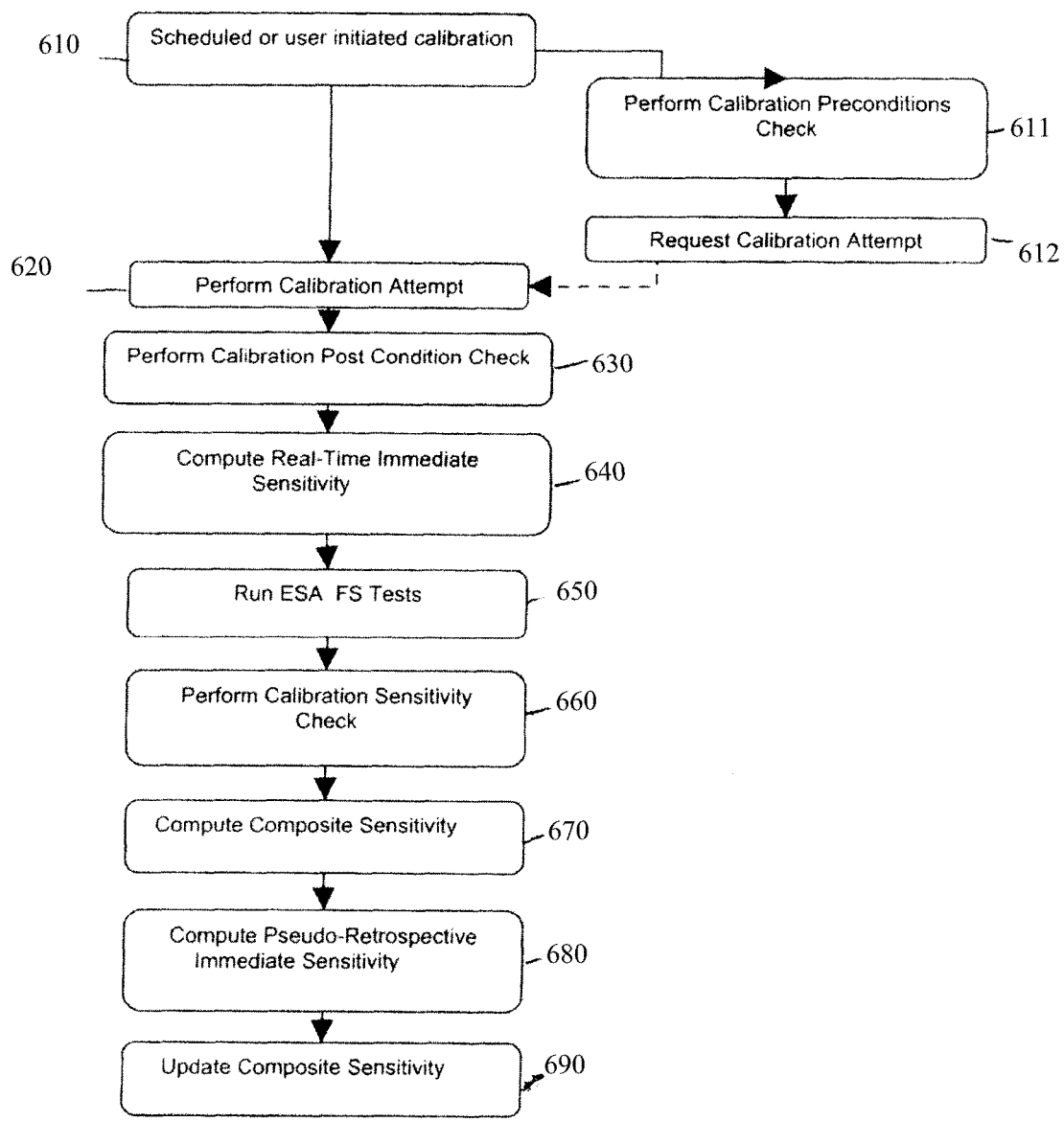
FIG. 6 is a flowchart showing in greater detail a sequence of steps that may be performed in certain embodiments in connection with calibration.

FIG. 6 is a flow diagram that outlines in further detail a number of phases for a calibration procedure in certain embodiments of the disclosed subject matter, particularly developed for continuous monitoring embodiments.

Figure 7:
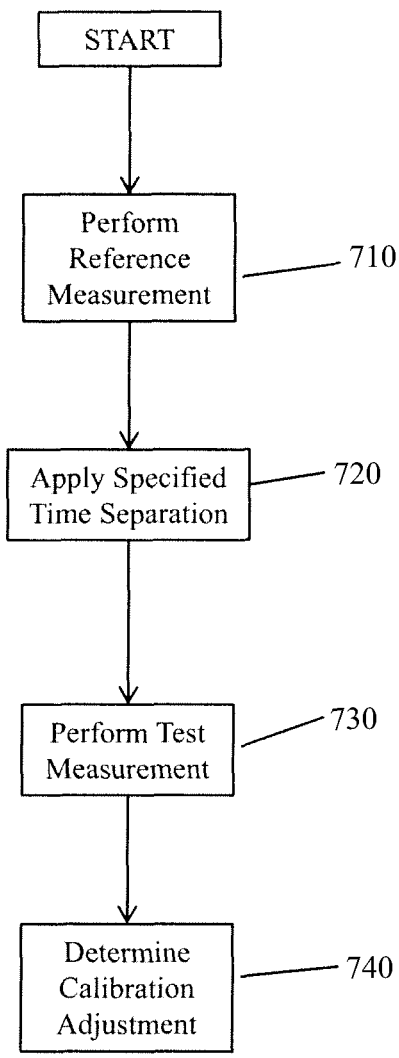
FIG. 7 is a flowchart illustrating a method for calibrating an on-demand analyte monitor.

In an on-demand system, certain adaptations will be introduced into the processing described in connection with FIG. 6, as well as in connection with FIG. 7, which follows. As will be seen, there are numerous calculations performed in connection with FIGS. 6 and 7 that contemplate a series of periodic or intermittent system measurements, as would normally be obtained during the operation of a CGM device. However, in an on-demand device, data processing unit 120 may communicate on separate, relatively widely spaced occasions, with receiver unit 140. Various techniques may be used to acquire, in an on-demand setting, the series of measurements contemplated by FIGS. 6 and 7, or to work around not having some or all of such data. For example, in embodiments in which data processing unit 120 includes storage for recent measurements, an on-demand calibration may invoke a bulk transfer of stored values, which may be sufficient to satisfy the requirements of the procedures envisioned by FIGS. 6 and 7. In other embodiments, the circuitry in data processing unit 120 may provide averaged and sequential data that may be used in a similar manner; although the sequenced data may provide fewer data points than might be used in a CGM counterpart performing the same procedures, the procedures could be performed with the fewer number of points. The circuitry could also provide rate of change measurements, e.g., by a differentiator circuit, or by comparison to a running average. Similarly, "retrospective" adjustments, as will be discussed, requiring a series of system measurements after a calibration, could similarly be provided by a follow-up on-demand measurement within a specified period of time. In addition, in some embodiments, e.g., where such data is not available, the calculations could proceed without the sequential data, using the last data acquired in place of an average, or not adjusting for rates of change where insufficient data is available to calculate those rates. A number of specific embodiments for acquiring periodic, averaged and/or rate-of-change measurements in an on-demand context are discussed below.

With the foregoing in mind, with regard to inherent differences between CGM and on-demand operating characteristics, the steps shown in FIG. 6 will now be addressed one-by-one in further detail, with reference to specific embodiments.

The calibration process in the illustrated embodiment begins with either a scheduled or user-initiated calibration (610). In these embodiments, analyte measurement system 100 expects calibration when either a scheduled calibration is due, or the user indicates intent to perform manual calibration, for example, by appropriate input into a CGM monitor, or alternatively by initiating an on-demand measurement.

The electrical current produced by analyte sensor 110, the temperature of the skin near the sensor, and the temperature of the circuitry may be checked for validity within data processing unit 120. Whenever data processing unit 120 is connected to receiver unit 140 (whether on a "continuous" basis or in an on-demand connection), these measurements and checks are transmitted to the receiver unit. In some embodiments, the data processing unit 120 transmits data to the receiver unit 140 via a "rolling data" field in a periodic data packet. Data may be spread out among consecutive data packets, and the packets may provide redundancy (and further reliability and data integrity) by accompanying current values with immediate past values. Other embodiments, e.g., in which the transmitter collects logged and/or time-delayed data, may transfer larger amounts of data with each transmission. See, e.g., U.S. patent application Ser. No. 12/807,278, filed on Aug. 31, 2010, which is hereby incorporated by reference herein in its entirety for all purposes. Data transmitted may include measurement calibration information and a "count" of the sensor measurement from an analog to digital converter (ADC).

After a calibration is initiated, a calibration preconditions check (611) may be performed. In one embodiment, these checks may include data validation on the transmitter side, including checks for hardware error (a composite OR of a plurality of possible error signals), data quality (set if the sensor measurement is changing faster than could be accounted for physiologically, indicative of an intermittent connection or leakage) and current/voltage saturation (compared to current and voltage thresholds). If any of these conditions are detected and then cleared, the corresponding flag bit remains set for a period, e.g., one minute, after the condition clears, to give time for the system to settle.

Further checks may be performed within receiver unit 140. A counter electrode voltage signal may be checked to ensure that it is within operating range, and if not the receiver processor may set a flag for invalid data not to be used for measurements (and hold the flag for a period, e.g., one minute, after the condition clears).

A data quality check may further comprise checks that all requisite data has been supplied by the transmitter; that none of the various error flags are set; and that the current and prior voltage counts were within prescribed limits (e.g., about 50-2900 voltage counts). There may be further validation that the transmitter temperature is in a valid range (e.g., about 25-40° C.), that raw sensor current is above an acceptable threshold (e.g., about 18 counts, minimum), and that sensor life state (provided by other logic in the system) is still active. There may also be a further check for high-frequency noise.

A data availability check may be performed. In this check, after eliminating points marked as invalid per the above-described processes, as well as those invalidated by upstream processes, a determination is made whether there are sufficient valid data points to reliably perform rate-related calculations, as may be required in various aspects of the calibration procedure. The data availability check may be varied for on-demand applications: they may be based on an examination of stored data received in the latest transmission (where the transmitter stores data or provides time-delayed data), or alternatively, these tests could be reduced or eliminated.

A minimum wait requirement check may be performed, to ensure that the calibration request does not conflict with the operative calibration schedule (As will be discussed, calibration scheduling imposes limitations on when calibrations may be taken and/or used, including waiting periods during baseline calibrations and at certain other times).

A sensor rate check may also be performed. A rate is calculated from a plurality of measurement points, based on a least-squares straight-line fit, again, where data is available. The value of the rate thus established must be less than the composite sensitivity (or if not yet calculated, a nominal sensitivity) multiplied by the sensor current.

Pre-calibration check procedures are further discussed in commonly assigned U.S. Publication No. 2008/0161666 and U.S. Publication No. 2009/0036747, which are hereby each incorporated by reference in their entirety herein for all purposes.

If conditions permit (or require) calibration, and calibration is called for or expected in accordance with a calibration schedule, or user initiated, a calibration attempt may be requested (612). Calibration "attempt" for purposes hereof means that a reference measurement is used or evaluated for calibration purposes. In some embodiments, requesting a calibration attempt comprises providing a prompt, for example, through a screen on receiver unit 140, or an audible prompt, to take a reference measurement, e.g., a BG fingerstick.

After the user has conducted a reference measurement for calibration (620), further checks may be performed, to check the sensor condition since the request for the reference test was made, and to ensure that the reference measurement is within an acceptable range (630). Such checks may further comprise the same tests as the pre-calibration checks, except that user interaction delays will not be factored into rate windows and determinations, and scheduling wait time constraints will not be considered (since the calibration has already started).

Post-calibration check procedures are further discussed in commonly assigned U.S. Publication No. 2008/0161666 and U.S. Publication No. 2009/0036747, referred to above.

After reference test data is acquired and checked, sensor sensitivity may be determined (640). Measured sensor current may be affected by a number of factors, for which appropriate corrections may be introduced.

As mentioned above in connection with FIG. 5, sensor current is also temperature dependent. The measurement of skin temperature can be influenced by the temperature of the environment around sensor 110 or on-body unit 101. To account for this dependence, analyte measurement system 100 may use two thermistors, one in the skin, and the other in the data processing unit 120 circuitry, to measure these temperatures, and then compensate.

A lag adjustment between interstitial fluid and blood glucose values may also be calculated. In comparing a measured interstitial analyte measurement with a blood-derived reference measurement, in a subject whose analyte level may be changing, there could be a time lag of the interstitial measurement as compared to the blood-based reference measurement, which could affect the accuracy of the calibration unless appropriately taken into account. In one embodiment, the lag corrected monitored data at the calibration time may be determined by applying the determined rate of change of the monitored data at the calibration time to a predetermined constant value. In one embodiment, the predetermined constant value may include, a predetermined time constant. For example, in one embodiment, the predetermined time constant may include a fixed time constant in the range of approximately four to fifteen minutes, and which may be associated with the one or more of the patient physiological profile, one or more attributes associated with the monitoring system (including, for example, but not limited to, the characteristics of the analyte sensor 110). In a further aspect, the predetermined time constant may vary based on one or more factors including, for example, but not limited to, the timing and amount of food intake by the patient, exogenous insulin intake, physical activities by the patient such as exercise, or any other factors that may affect the time constant, and which may be empirically determined. See U.S. Publication No. 2008/0081977, now U.S. Pat. No. 7,618,369, which is hereby incorporated herein by reference in its entirety for all purposes. Where only fewer data points are available, other rate calculations may be used. In addition, analog rate measurements may be made and transmitted as separate measurements.

In certain embodiments, signal attenuation may also affect sensor readings. "Early Signal Attenuation" (ESA) refers to a condition in which the effective signals representing an analyte level measured by a sensor appears to attenuate and then recover in the early stages of the sensor life. For example, for some embodiments, the sensor signals of the system may attenuate during the first 24 hours after insertion. Some embodiments employ one or more procedures to detect this state to avoid giving inaccurate readings while the system is in an ESA condition. The states that may be defined with respect to ESA, and the transitions between those states, are discussed below in connection with calibration scheduling. As will be further addressed in that discussion, ESA detection may be performed (650), in some embodiments, primarily during periods in which ESA is likely to occur, e.g., within the first 24 hours after insertion. ESA detection procedures are further described in commonly assigned U.S. patent application Ser. No. 12/363,712, now U.S. Pat. No. 8,346,335, which is hereby incorporated by reference in its entirety herein for all purposes.

In certain embodiments, two calibration sensitivity tests are performed (660) after passing the ESA tests described above: an absolute test, and a relative (outlier) test. In the absolute sensitivity test, the measured immediate sensitivity is compared to the nominal sensitivity for the sensor. The relative sensitivity test is intended to eliminate "outlier" measurements from being used to calculate composite sensitivity. As will be discussed in the next section, a composite sensitivity calculation, in some embodiments, requires two sensitivity figures, S1 and S2. $S_{i(k)}$, $S_{i(k-1)}$, and $S_{i(m)}$ are chosen in connection with ESA. If $S_{i(k)}/S_{i(k-1)}$ (e.g., current valid sensitivity compared to preceding valid sensitivity) is in the range of about 0.778 to 1.5, then $S_{i(k-1)}$ (the prior value) will be used as S1, and $S_{i(k)}$ (the current value) will be used as S2. If the foregoing test fails, then, if there is an S(m) established, and if $S_{i(k)}$ compared to the previously determined composite sensitivity (Sc) falls within the above range, then $S_{i(m)}$ will be used for S1 and $S_{i(k)}$ will be used as S2. Otherwise, another calibration attempt is requested, for which $S_{i(k)}$ will become $S_{i(k-1)}$, and as part of the new determination, the relative (outlier) test will be repeated. These procedures are further described in commonly assigned U.S. Publication No. 2009/0036747, which is hereby incorporated by reference in its entirety herein for all purposes.

The computed composite sensitivity (670), $S_c$, is used to convert sensor current in units of ADC counts to calibrated analyte (e.g., glucose) levels in units of mg/dL in some embodiments. For the first calibration, the composite sensitivity is equal to the sensitivity from a single valid calibration attempt. When appropriate thereafter, multiple sensitivities are used to determine the composite sensitivity.

For the first calibration, the composite sensitivity takes the value of $S_{i(k)}$. Afterwards, the composite sensitivity is a weighted average of the $S_1$ and $S_2$ values determined by the outlier check:

$$S_c(k)=S_1 W_1+S_2 W_2$$

The first weighting parameter and the second weighted parameter may be different or substantially equal. They may, for example, be one or both of time based, or based on a prior calibration parameter. In certain embodiments, the weighing factors used are about 0.4, 0.42, 0.433, 0.444, etc. for $W_1$, and 0.6, 0.58, 0.567, 0.556, etc. for $W_2$. In some embodiments, the weighting factors may depend upon when the analyte measurement was taken, e.g., more recent analyte measurements may be assigned a larger weighting factor.

$S_c$ may need to be updated between calibrations, as a result of a pseudo-retrospective immediate sensitivity adjustment, in which case $S_2$ will be replaced with a new value from that adjustment.

During operation of receiver unit 140, a calibrated analyte concentration figure ($G_{CAL}$) may be obtained using the currently valid composite sensitivity:

$$G_{CAL}=G_{rTC}/S_C$$

The latest immediate sensitivity value $S_2$ used to calculate composite sensitivity incorporates, as discussed, a lag correction to take into account the delay between a change in blood analyte level and a corresponding change in the interstitial level of the analyte. However, if analyte levels continue to change after a calibration, it may be possible, in some embodiments, to improve the lag correction by factoring in system measurements taken after the calibration, and use the improved correction to update $S_2$, and, correspondingly, $S_c$. This correction is based on subsequent system measurements, and accordingly may be done without taking a new reference measurement (e.g., fingerstick).

In certain embodiments, this correction, referred to as a pseudo-retrospective immediate sensitivity correction (680), is calculated after about seven system measurements have been taken after the prior calibration (provided no subsequent calibration attempt becomes eligible for update before this number of system measurements have been collected), of which at least about four are valid. Alternatively, the retrospective data could be provided by a subsequent on-demand system measurement. If the standard error associated with computing the adjusted analyte count is less than the standard error in the underlying lag correction calculation (e.g., an improved correction is indicated), the sensitivity used for $S_2$ may be updated accordingly.

To perform the correction, a new least-squares fitted line may be determined, taking into account the additional post-calibration data system measurements, and the slope (rate) and intercept of this line used to calculate a corrected value ($G_{PrLrTC}$) for the real time value $G_{RtLrTC}$, which may be divided by the reference measurement from the latest attempt to obtain an updated sensitivity to use as $S_2$.

These procedures for calculating a pseudo-retrospective immediate sensitivity correction are further described in commonly assigned U.S. Publication No. 2008/0081977, now U.S. Pat. No. 7,618,369, which is hereby incorporated by reference in its entirety herein for all purposes.

As noted, if a pseudo-retrospective immediate sensitivity correction is performed, resulting in an updated value for $S_2$, then a corresponding update composite sensitivity factor, $S_c$, may be calculated (690). The value of $S_1$ used in the earlier calculation of $S_c$ will continue to be used.

Further description of the procedures outlined in FIG. 6 can be found in, for example, U.S. Publication No. 2009/0005665, now U.S. Pat. No. 8,444,560; U.S. Publication No. 2008/0288204; U.S. Publication No. 2009/0006034; U.S. Publication No. 2008/0255808, now U.S. Pat. No. 8,140, 142; U.S. Publication No. 2008/0256048; U.S. Publication No. 2009/0006034; U.S. Publication No. 2008/0312842, now U.S. Pat. No. 8,239,166; U.S. Publication No. 2008/

0312845; U.S. Publication No. 2008/0312844, now U.S. Pat. No. 7,996,158; U.S. Publication No. 2008/0255434; U.S. Publication No. 2008/0287763; U.S. Publication No. 2008/0281179; U.S. Publication No. 2008/0288180, now U.S. Pat. No. 8,260,558; U.S. Publication No. 2009/0033482, now U.S. Pat. No. 7,768,386; U.S. Publication No. 2008/0255437; and U.S. Publication No. 2009/0036760. Each of these disclosures are hereby incorporated in its entirety herein for all purposes.

In some embodiments, filtering may be performed before the analyte level is displayed. In an on-demand setting, filtering may be accomplished by using analog-averaged values, or by performing calculations for a series of stored values transmitted as a batch and filtering those values as above.

On-demand monitors will generally not automatically perform system measurements after a discrete calibration attempt, because such monitors inherently rely on the user to initiate a system measurement, e.g., by bringing receiver unit 140 into proximity of on-body unit 101 and/or providing a user input, such as pressing a button. Referring to FIG. 7, an adapted calibration approach may be used with an on-demand monitor.

The system causes a reference measurement of a level of said analyte in the subject to be performed by a method other than use of the system being calibrated (710). The system causes the user to use the on-demand system to perform at least one test measurement of a level of said analyte (730), within about a specified period before or after the time of the reference measurement (720). The system determines a calibration adjustment, as a function of at least said reference measurement and said at least one test measurement (740). The reference measurement in the foregoing protocol could be caused to be conducted at a time in accordance with a calibration schedule for the in-demand device.

An optional method for sensor calibration may comprise the following steps: (a) factory determination of sensor sensitivity, (b) factory assignment of sensor calibration number, (c) user enters factory calibration number into on-demand RX, (d) on-demand Tx measurement of sensor current and temperature, and (e) software in RX determines corrected glucose.

Figure 8A:
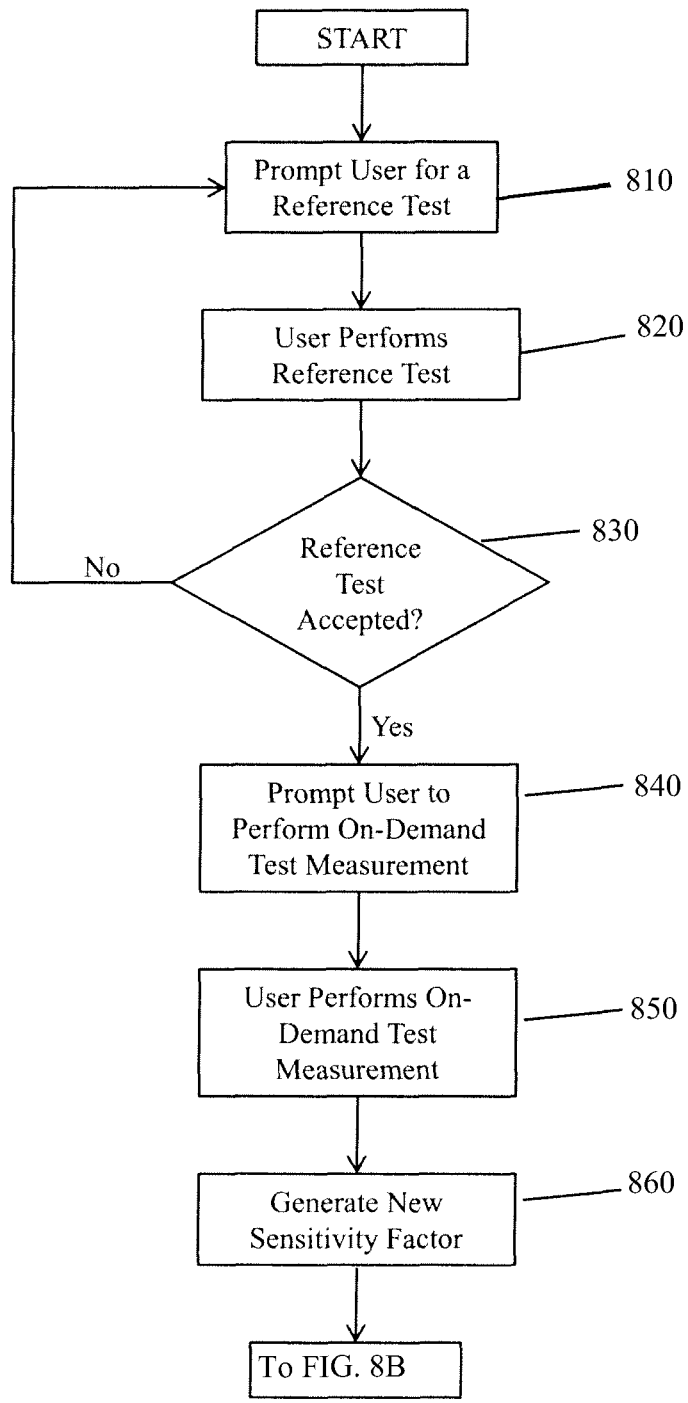
FIGS. 8A-8B is a flowchart illustrating further calibration steps that may be performed in an on-demand analyte monitor.
Figure 8B:
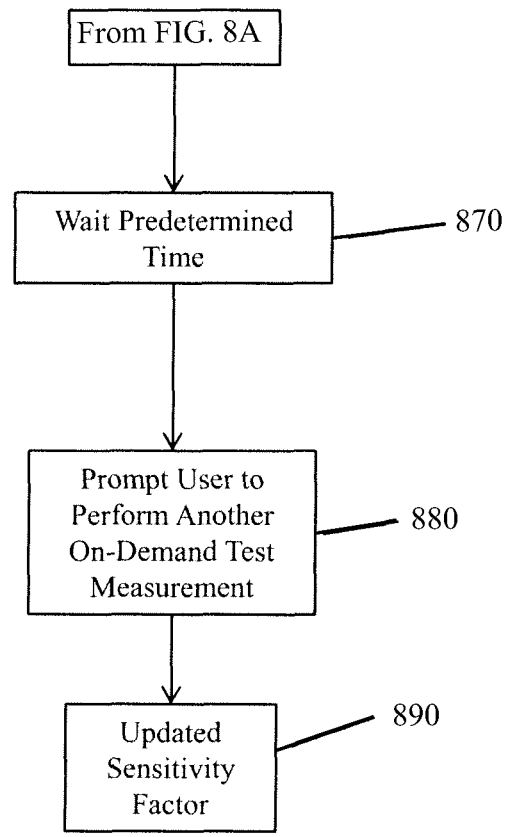

For calibration schemes where sensor data prior to and substantially proximate to the calibration BG reading are used in the sensitivity calculation, a more detailed adapted calibration procedure could be used as shown in FIGS. 8A and 8B. The receiver unit 140 may prompt the user for a reference test (810). The user some time later performs a reference test (820). If the calibration logic in the receiver unit accepts the reference measurement for calibration (830), then the receiver unit may prompt the user to acquire an "on-demand" test result with the device (840). The user some time later performs the on-demand test measurement, e.g., by bringing the receiver unit into proximity with the transmitter device so as to induce a test measurement to be taken (850). The receiver unit processes the reference measurement and test measurement taken on demand to generate a new sensitivity factor for calibration of the system (860).

The foregoing procedure differs from a CGM calibration procedure, e.g., in its prompts and in how the on-demand test measurement is acquired. In a CGM implementation, the CGM data may be acquired continuously or intermittently, and are typically available prior to the reference measurement.

A variation of the above procedure might be employed where an on-demand measurement is acquired prior to but recent to the reference measurement. In such a case, the system may check for this and not prompt the subject, and use the on-demand measurement that had already been acquired. Alternatively, the procedure may not use an explicit prompt, but the user could be instructed to perform the on-demand test measurement without the prompt. Furthermore, the receiver unit could provide the option of whether to include the prompt or not.

The on-demand test measurement may include one or more sensor measurements. These measurements may be temporal signal samples in the past, lagged measurements of the sensor signal such as can be achieved by measuring the same signal lagged by an RC circuit, or any other form of signal measurements including measurement of multiple signals. For example, sensor temperature may also be measured. As previously mentioned, specific embodiments for acquiring periodic, averaged and rate-of-change data from a transmitter device in the context of an on-demand measurement are discussed further below.

Some CGM calibration protocols use sensor data acquired prior to, substantially proximate to, and after the reference test reading in the sensitivity calculation. For example, in some embodiments, CGM data subsequent to a BG reading may be used to improve the lag correction included in the calibration method. Such data may be used to update the calibration at some time, for example about seven minutes, after the BG reading.

In certain embodiments, additional steps may be implemented to increase the accuracy of the calibration. After the new sensitivity factor is generated (860), after a predetermined time after the reference measurement (870), the receiver unit prompts the user to acquire another on-demand test measurement (880). The receiver unit uses the newly acquired on-demand test measurement to generate an updated sensitivity factor (890). This process may use the previously acquired on-demand data and reference measurement, or only the previous sensitivity results; other processing variations are possible as appropriate.

If the on-demand system has the capability of transmitting periodic, averaged or rate-of-change information based on a sequence of measurements preceding the on-demand transmission, then that additional data will be available for use in connection with the above-described update, to further refine the update.

As discussed above, prompts are provided to the user to perform a reference analyte measurement. In some embodiments, if the user does not perform the reference measurement within a grace period, the system will not provide sensor readings until the next calibration measurement is performed. Similarly, if a requested calibration is failed, for any number of reasons (e.g., glucose outside of desirable range for calibration), the system will not accept the blood glucose measurement as a valid calibration and will not provide sensor readings and may prompt the user to perform additional calibration attempts.

As a result, the timing of the calibration requests can be unpredictable, which can be frustrating to the user of the system. Calibration requests that frequently repeat or that occur during a fixed schedule may occur at inopportune times. A technique is provided which imposes limits on the system calibration requests to make the calibration algorithm more user-friendly.

Figure 9:
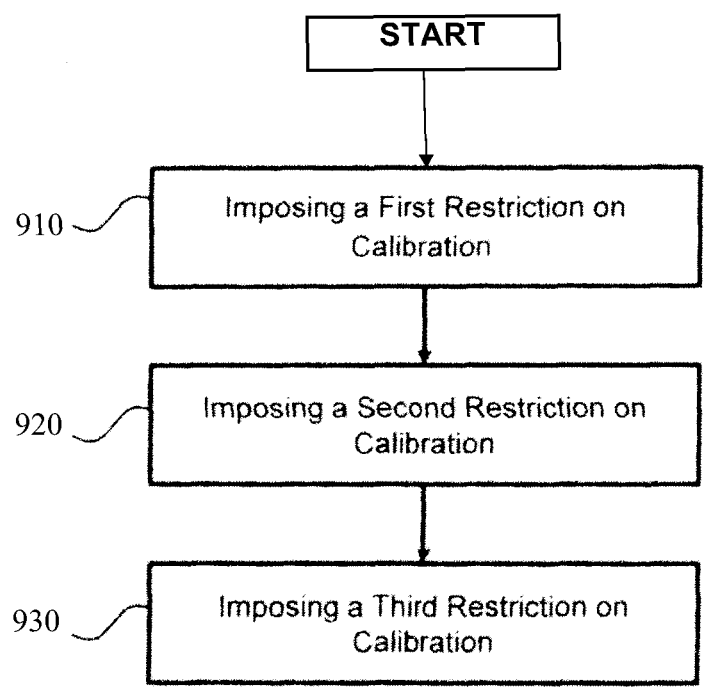
FIG. 9 is a flowchart illustrating calibration steps in an analyte monitor in accordance with one embodiment of the present disclosure.
Figure 10:
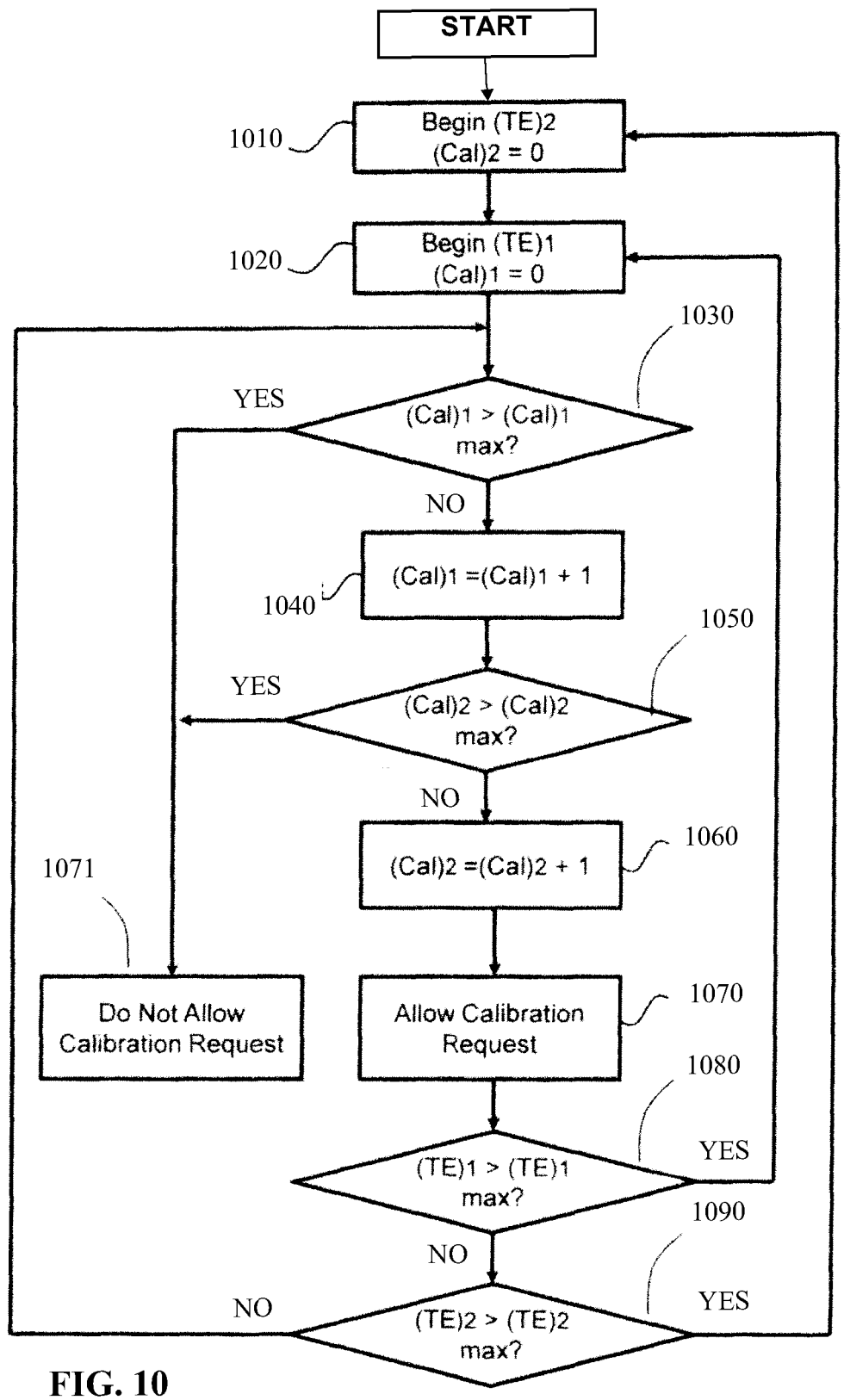
FIG. 10 is a flowchart illustrating calibration steps in an analyte monitor in accordance with an embodiment of FIG. 3 of the present disclosure.

As illustrated in FIGS. 9 and 10, the system imposes a first limitation (910) on the frequency of calibration requests in some embodiments. The first calibration request limitation is to put a cap on the frequency of repeated calibration requests in a given time frame. In one embodiment, this limitation can be posed as two nested time windows. For the first level, there can be no more than $(Cal)_1$ max calibration requests in any time period $(TE)_1$. For example, no more than 1 request per hour. For example, it is believed that repeated measurements within a short time frame do not provide as much new glucose information to the user, since the blood glucose change in a short period of time is limited by physiology. As illustrated in FIG. 10. Time period $(TE)_1$ begins to run and Max calibration request counter $(Cal)_1$ begins to run (1020). If the number of calibration requests $(Cal)_1$ exceeds the maximum number of calibration requests $(Cal)_1$ max (1030), calibration requests are not allowed (1071). If the number of calibration requests does not exceed the maximum number of calibration requests, $(Cal)_1$ is incremented (1040).

The second level is a cap on the number of calibration requests issued in a longer period of time $(TE)_2$, such as a day. In some embodiments, the second time period may be derived from a reasonable assessment of the limit in the number of blood glucose measurements a user would typically be willing to perform in a given day in the absence of continuous glucose monitoring. As illustrated in FIG. 10, time period $(TE)_2$ begins to run and Max calibration request counter $(Cal)_2$ begins to run (1010). If the number of calibration requests $(Cal)_2$ exceeds the maximum number of calibration requests $(Cal)_2$ max (1050), calibration requests are not allowed (1071). If the number of calibration requests does not exceed the maximum number of calibration requests, $(Cal)_2$ is incremented (1060). If the number of calibration requests $(Cal)_2$ does not exceed the maximum number of calibration requests $(Cal)_2$ max (1050) and the number of calibration requests $(Cal)_1$ does not exceed the maximum number of calibration requests $(Cal)_1$ max (1030), calibration requests are allowed (1070). When the first time period $(TE)_1$ expires (1080) or the second time period $(TE)_2$ expires (1090), the values are reset.

Figure 11:
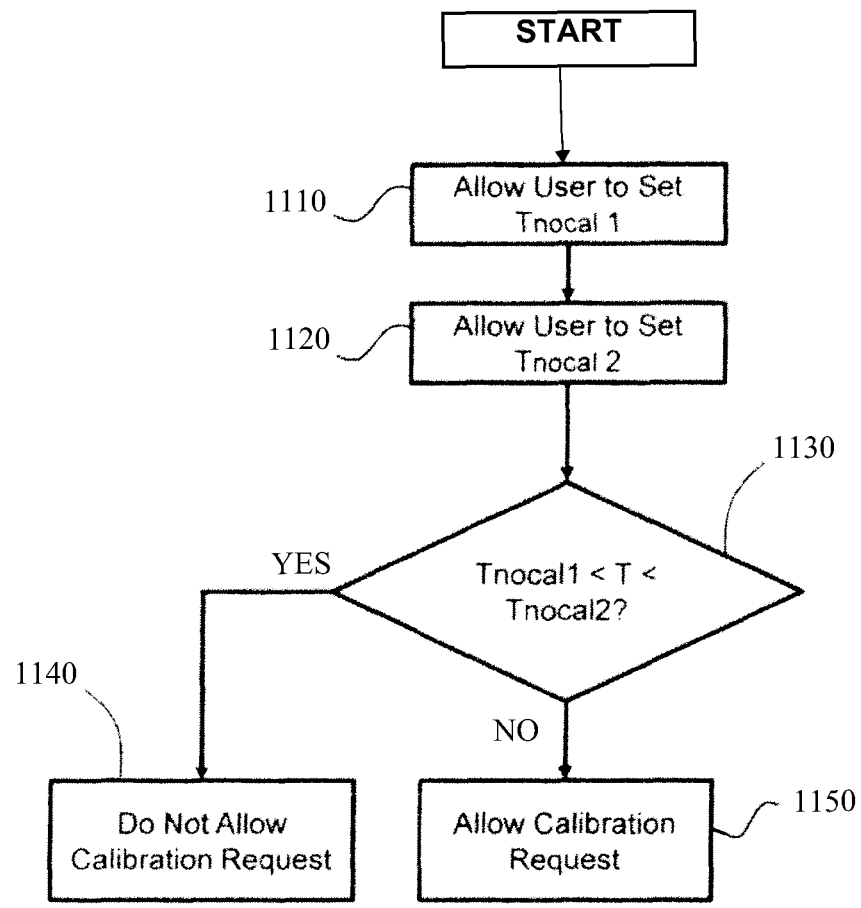
FIG. 11 is a flowchart illustrating calibration steps in an analyte monitor in accordance with an embodiment of FIG. 3 of the present disclosure.

As illustrated in FIG. 9, the system imposes a second limitation (920) on the frequency of calibration requests in some embodiments. The second restriction on calibration requests is to prevent or further limit calibration requests during periods of time when the user is likely to be sleeping, for example, when the system time is between 10 PM and 8 AM. In different embodiments, this time range may or may not be set by the user. Calibration requests during these periods may have a very negative effect on the user experience, and so the possible loss in data that can occur if the calibration expires at night may be offset by the gain in user satisfaction. As illustrated in FIG. 11, the user is provided with the opportunity to set the beginning of the time period in which calibration requests are not allowed $(T_{nocal})_1$ (1110). The user is provided with the opportunity to set an end of the time period in which calibration requests are not allowed $(T_{nocal})_2$ (1120). If the system determines that current time T is within the selected time period (1130), then calibration requests are not allowed (1140). If the current time T is outside the selected time period, calibration requests are allowed (1150).

Figure 12:
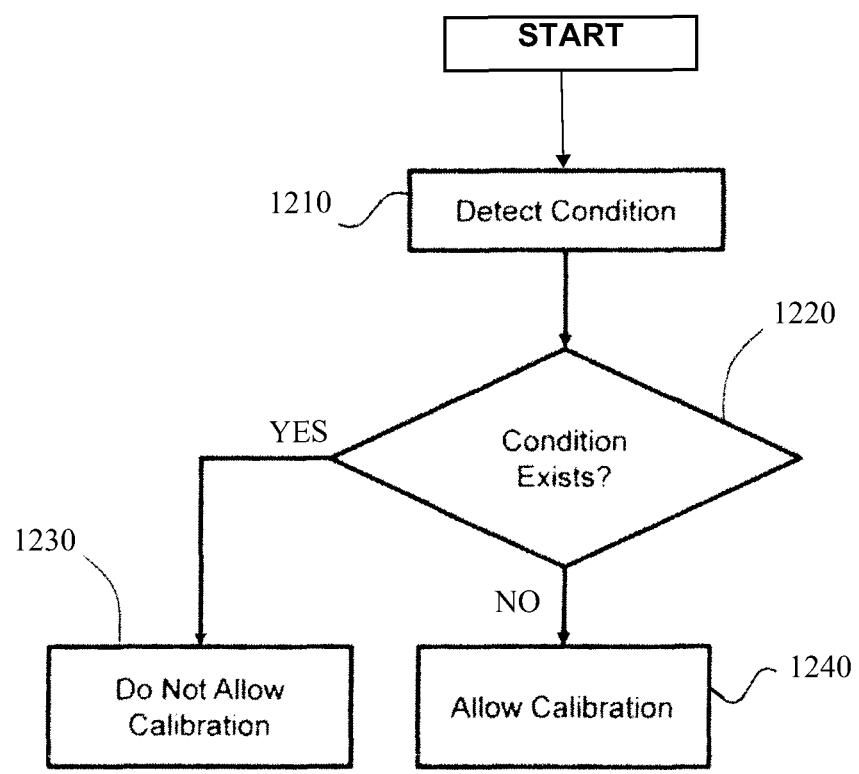
FIG. 12 is a flowchart illustrating calibration steps in an analyte monitor in accordance with an embodiment of FIG. 3 of the present disclosure.

As illustrated in FIG. 9, the system imposes a third limitation (930) on the frequency of calibration requests in some embodiments. The time range for preventing or limiting calibration requests may incorporate mechanisms to dynamically detect that a condition exists, e.g., that a user is sleeping, so as to further improve the user experience. This determination may involve such things as temperature data, e.g., skin surface temperature, measured by the transmitter, appearing to rise during sleep (perhaps due to blankets), glucose data, e.g., characteristic glucose patterns such as dawn phenomenon and symogyi effect that could be indicative of sleep, frequency of interaction with the receiver (e.g. button pushes), e.g., reduced interaction with device during sleep, relative position of the device, e.g., prolonged orientation of the device in a horizontal position, acceleration measurements, e.g., detecting motion (or lack of motion) indicative of sleep, or other measures that may be indicative of sleep. As illustrated in FIG. 12, the system determines whether the condition exists (1210). If the condition exists (1220), then calibration requests are not allowed (1230). If the condition does not exist, calibration requests are allowed (1240).

In certain embodiments, conditions other than sleeping may be detected. For example, during periods of activity, such as during exercise, calibration may be inconvenient to the user and further, calibration during such times may be inaccurate. The system may detect conditions associated with such bodily conditions, such as by monitoring body temperature, blood pressure or the pulse of the user. In certain embodiments, a user or a user's physician or care provider may have the option of programming particular bodily parameters associated with conditions during which time calibration is not to be requested.

In further embodiments, calibrations are performed at times determined by the user, in addition to or in substitution of, the pre-set calibration schedule. Such user-determined calibration may take into account that there are particular times of day where it is optimal for the user to calibrate. For example, exemplary optimal times to calibrate can include in the morning before leaving the house for work, or at night before going to bed.

In some embodiments, the user-determined calibration can require that the user take some action to calibrate on a user-determined schedule. If the user takes no action, then the system defaults to the pre-set calibration schedule.

When the user uses a user-determined calibration schedule, the algorithm typically adjusts the pre-set calibration schedule (e.g., if the calibration occurred after the first day, the next pre-set calibration would be scheduled to occur 48 hours after the just completed user-determined calibration).

Figure 13:
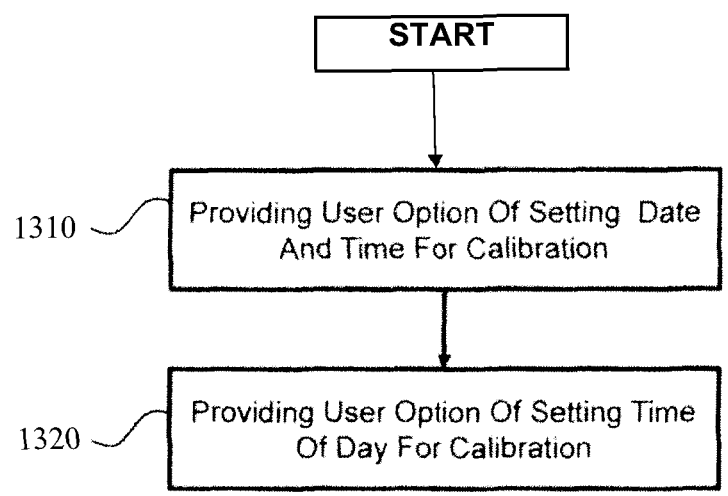
FIG. 13 is a flowchart illustrating calibration steps in an analyte monitor in accordance with one embodiment of the present disclosure.

As illustrated in FIG. 13, a first user-determined calibration mode includes a user-configurable calibration time. According to this mode, a user can schedule their upcoming calibrations. Two exemplary variations of this method are proposed.

In the first variation, the user schedules the date and time of 1 to n calibrations in advance (1310). In this variation, the user could access a screen on the receiver unit that showed the upcoming calibration times. The user would be allowed to edit or delete these times (within the rules of the algorithm as discussed herein) and would be allowed to add new times.

In the second variation, the user sets 1 to 2 times of days when they want to calibrate (1320). For each time, the user would be allowed to specify whether that calibration was to occur daily or every 2 days.

Figure 14:
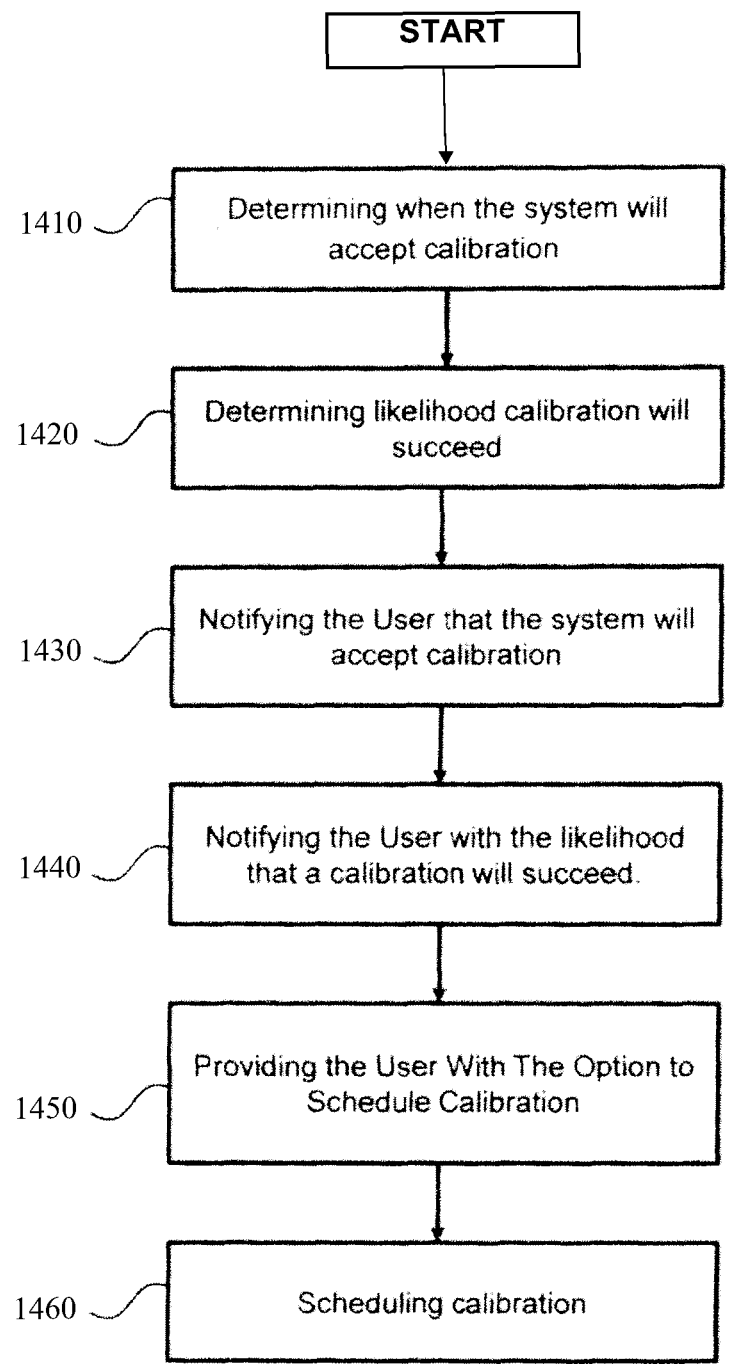
FIG. 14 is a flowchart illustrating calibration steps in an analyte monitor in accordance with one embodiment of the present disclosure.

As illustrated in FIG. 14, the system determines when it will accept calibration (1410). In some embodiments, accepting calibration is distinguished from an indication that a calibration is required. For example, in some embodiments, meaningful calibration may be accepted as frequently as 15 minutes apart, 30 minutes apart, an hour apart, etc. In some embodiments, two calibrations per day (every twelve hours) are permitted. In some embodiments, a calibration pre-check is incorporated having a low threshold for failure on rate of change. Further details are provided in U.S. Patent Publication No. 2008/0161666, filed Dec. 29, 2006, entitled "Analyte Devices and Methods," which is incorporated by reference in its entirety herein.

When the system will accept a calibration, the user is notified (1430). According to some embodiments, an icon or some other indicator is added to the system that notifies the user. The system may also determine the likelihood that a calibration will succeed (1420). The system provides the user with the likelihood that the calibration will succeed (1440). Additionally a color coded icon could be used in some embodiments to indicate the likelihood that a calibration will succeed. After providing the notifications, the system provides the user with the option of scheduling calibration (1450). If the user elects to calibrate, such calibration is scheduled (1460).

In some embodiments, calibrations are required to occur at one or more scheduled calibration time(s). For example, preset intervals may be provided, e.g., that calibration occurs at 24 hours, 48 hours, and 72 hours after sensor insertion, etc. In other embodiments, scheduled calibration times may be every 12 hours after sensor insertion. A grace period may be provided after the scheduled calibration time of about, e.g., about 30 minutes, about one hour, about 90 minutes. A grace period of about 2 hours, about 6 hours, about 8 hours, about 12 hours, etc., is provided for subsequent attempts in certain embodiments. An alarm may be provided to the user if no calibration occurs at either scheduled calibration time, or at the expiration of the grace period to require the user to perform the calibration.

A user may take a reference analyte measurement at various times during the use of the system. However, the reference analyte measurement is typically not accepted for calibration except during these schedule calibration times and the subsequent grace period.

Figure 15:
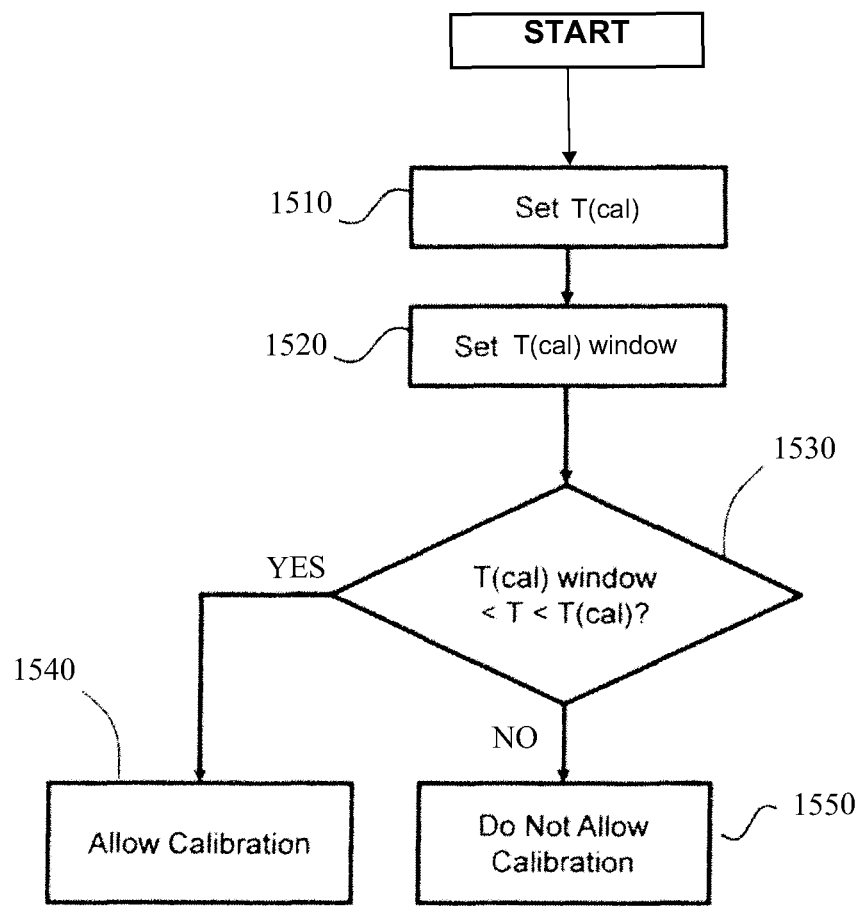
FIG. 15 is a flowchart illustrating calibration steps in an analyte monitor in accordance with one embodiment of the present disclosure.

In some embodiments, a time window is provided preceding the scheduled calibration time. As illustrated in FIG. 15, the system sets a predetermined scheduled calibration time T(cal) (1510). The system may also set a time which corresponds to the beginning of the calibration window T(cal)$_{window}$, e.g., 10 minutes, 30 minutes, one hour, etc., before the scheduled calibration time (1520). The system determines whether the current time T is within the window (1530), and if the current time is within the window, the system will allow calibration (1540). If the current time is not within the window, the system will not allow calibration (1550).

In some embodiments, if a reference analyte measurement is available, the system accepts the measurement for calibration if the current time T is within the calibration window. In some embodiments, the system provides an indication (e.g., visual or audible) that calibration will be accepted, regardless of whether a reference analyte measurement is available.

If the user provides a reference analyte measurement, such as a finger stick during the calibration window and calibrates the system, the alarm is suppressed that normally sounds if no calibration occurs at the predetermined calibration time or within the grace period.

Figure 16:
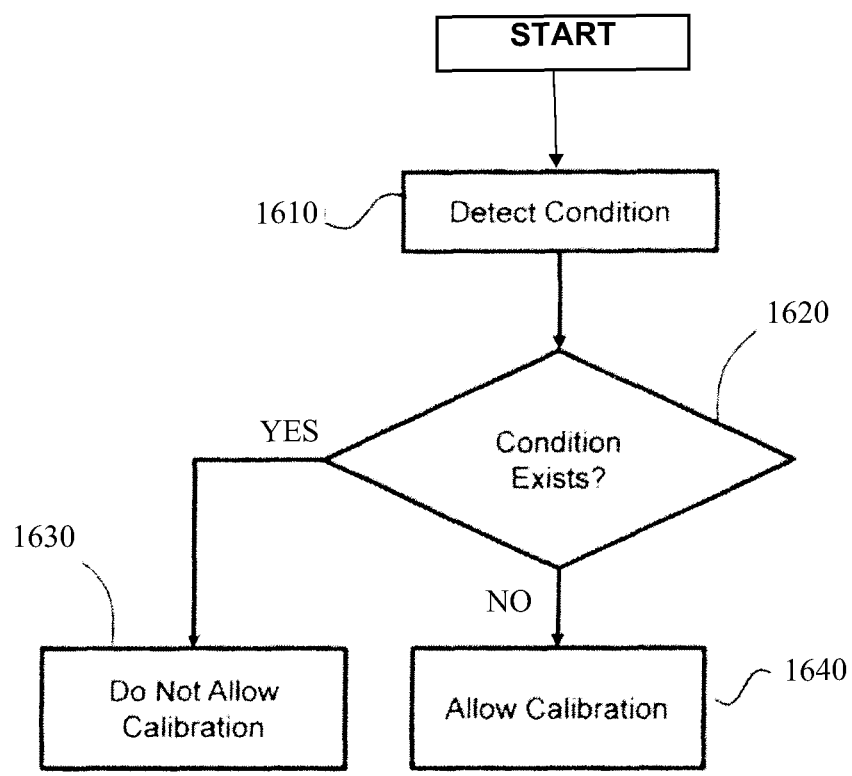
FIG. 16 is a flowchart illustrating calibration steps in an analyte monitor in accordance with one embodiment of the present disclosure.

In some embodiments, the system requests calibration based upon the stability of the sensor signal over time. Thus, as illustrated in FIG. 16, the system incorporates logic to dynamically detect that a particular condition exists (1610). For example, the system may detect that the absolute rate of change of the sensor signal is less than 1 mg/dL/min. In the initial hours after sensor insertion, e.g., 2 hours, 10 hours, 12 hours, etc., this would also require that the on-line "ESA detection and identification" module show high probability, e.g., 90%, 95%, etc., that the sensor performance had stabilized. See, e.g., U.S. patent application Ser. No. 12/363,712, now U.S. Pat. No. 8,346,335, which is hereby incorporated by reference in its entirety herein for all purposes. In some embodiments, stability sensing operates as a detector of a hypoglycemic condition. For example, when low glucose is detected during the period of time where instability in the sensor signal is typically observed, an alarm is presented and the user must perform a fingerstick to either confirm the instability in the sensor signal or to identify the condition as a true hypoglycemic event. If the condition exists (1620), the system may not allow calibration (1630) and if the condition does not exist, calibration is allowed (1640).

In the event of an apparent rapid sensor equilibration before a first time period, e.g., about four hours, the receiver would then prompt the user to do an additional calibration measurement subsequently, e.g., at about two hours, four hours, six hours, ten hours, twelve hours, etc.

Furthermore, the logic within the system may operate to cause the user to perform an additional system measurement, some time after the first or prior system measurement, for example, five minutes, or seven minutes, or ten minutes, or some other period after, and could provide functions to update the system calibration adjustment based on the additional system measurement. The updated calibration adjustment may be calculated by the logic as a function of at least the additional system measurement, the prior system measurement and the reference measurement. Alternatively, the updated calibration adjustment may be calculated by the logic as a function of the additional system measurement and a prior calibration adjustment.

Additionally, the system measurements used by the logic for calibrating device may comprise temporal signal samples acquired in the past, or time-lagged measurements of the sensor signal, such as may be obtained from a RC network coupled to an analyte sensor. Furthermore, the logic could provide for incorporating other measurements, such as skin and sensor temperature measurements, which could be acquired individually or as part of a data transmission from transmitter device containing multiple measurements.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in U.S. patent application Ser. No. 10/745,878 filed Dec. 26, 2003, now U.S. Pat. No. 7,811,231, entitled "Continuous Glucose Monitoring System and Methods of Use", each assigned to the Assignee of the present application, and each of which are incorporated herein by reference for all purposes.

In certain embodiments, a method for calibrating a signal from an electrochemical sensor may comprise generating a signal from the sensor, the signal corresponding to an analyte concentration level in a biofluid of a subject, prompting a user to assay a calibration sample of the user's blood to obtain a calibration value, if a first condition is met, and correlating the calibration value to at least one of the signals from the sensor if the first condition of is met.

Certain aspects may include selecting a first time frame.

Certain aspects may include selecting a maximum number of calibrations in the first time frame.

In certain aspects, the first condition may be met if fewer than the maximum number of calibrations have occurred in the first time frame.

Certain aspects may include selecting a second time frame.

Certain aspects may include selecting a maximum number of calibrations in the second time frame.

In certain aspects, the first condition may be met if fewer than the maximum number of calibrations have occurred in the second time frame.

Certain aspects may include prompting the user to assay a calibration sample of the user's blood to obtain a calibration value, if a second condition is met.

Certain aspects may include allowing the user to select a time period in which calibrations are not accepted.

In certain aspects, the second condition may be met if the current time is outside the selected time period.

Certain aspects may include prompting the user to assay a calibration sample of the user's blood to obtain a calibration value, if a third condition is met.

Certain aspects may include determining the existence of a condition relating the subject.

In certain aspects, the condition may include a determination of whether the subject is asleep.

In certain aspects, the third condition may be met if the condition does not exist.

In certain embodiments of the present disclosure, a method for calibrating a signal from an electrochemical sensor may comprise generating a signal from the sensor, the signal corresponding to an analyte concentration level in a biofluid of a subject, providing a user the option to select a time for obtaining a calibration sample of the user's blood to obtain a calibration value, and correlating the calibration value to at least one of the signals from the sensor if the current time corresponds to the selected time.

In certain aspects, providing a user an option to select a time may include providing a user the option to select a date and a time for calibration.

In certain aspects, providing a user an option to select a time may include providing a user the option to select a time for recurrent daily calibration.

In certain embodiments of the present disclosure, a method for calibrating a signal from an electrochemical sensor may include generating a signal from the sensor, the signal corresponding to an analyte concentration level in a biofluid of a subject, determining whether calibration is accepted, providing a user the option to obtain a calibration sample of the user's blood to obtain a calibration value if calibration is accepted, and correlating the calibration value to at least one of the signals from the sensor.

In certain aspects, the predetermined time may be fifteen minutes

In certain aspects, the calibration may be accepted if the rate of change of the signal is within a predetermined threshold.

Certain aspects may include determining the likelihood of successful calibration.

In certain aspects, an icon may be provided in a display unit relating to the likelihood of successful calibration.

In certain embodiments, a method for calibrating a signal from an electrochemical sensor may include generating a signal from the sensor, the signal corresponding to an analyte concentration level in a biofluid of a subject, determining a predetermined calibration time, determining a prospective calibration window running prior to the predetermined calibration time, and allowing calibration if a reference analyte measurement is available during the prospective calibration window.

Certain aspects may include providing a grace period after the predetermined calibration time, and providing an alarm if no calibration is performed during the time period beginning with the predetermined calibration time and ending with the expiration of the grace period.

Certain aspects may include suppressing the alarm if a reference analyte measurement is available during the prospective calibration window.

Certain aspects may include notifying the user if a reference analyte measurement is being accepted for calibration.

In certain aspects, the prospective calibration window may include a time period of 10 minutes prior to the predetermined calibration time.

In certain aspects, the prospective calibration window may include a time period of 30 minutes prior to the predetermined calibration time.

In certain aspects, the prospective calibration window may include a time period of one hour prior to the predetermined calibration time.

In certain embodiments, a method for calibrating a signal from an electrochemical sensor may include generating a signal from the sensor, the signal corresponding to an analyte concentration level in a biofluid of a subject, determining a condition relating to the stability of the sensor signal, and allowing calibration if the sensor stability is within a predetermined threshold.

In certain aspects, the predetermined threshold may include a sensor stability of about 1 mg/dL/min.

Certain aspects may include determining a duration of sensor operation and determining stability of the sensor signal at a reference duration of sensor operation.

Certain aspects may include requesting a calibration if the stability of the sensor signal at the reference duration of sensor operation is below a threshold.

In certain aspects, the reference duration of sensor operation may include an elapsed time following insertion of the sensor in the subject.

In certain aspects, the reference duration may include four hours.

In certain embodiments, an analyte measurement system may include an electrochemical sensor generating a signal corresponding to an analyte concentration level in a biofluid of a subject, and a processor unit comprising a user interface for prompting a user to assay a calibration sample of the user's blood to obtain a calibration value, if a first condition is met; and configured to correlate the calibration value to at least one of the signals from the sensor if the first condition of is met.

In certain aspects, the user interface may provide an option for selecting a first time frame.

In certain aspects, the user interface may provide an option for selecting a maximum number of calibrations in the first time frame.

In certain aspects, the first condition may be met if fewer than the maximum number of calibrations have occurred in the first time frame.

In certain aspects, the user interface may provide an option for selecting a second time frame.

In certain aspects, the user interface may provide an option for selecting a maximum number of calibrations in the second time frame.

In certain aspects, the first condition may be met if fewer than the maximum number of calibrations have occurred in the second time frame.

In certain aspects, the user interface may be configured to prompt the user to assay a calibration sample of the user's blood to obtain a calibration value, if a second condition is met.

In certain aspects, the user interface may provide an option for allowing the user to select a time period in which calibrations are not accepted.

In certain aspects, the second condition may be met if the current time is outside the selected time period.

In certain aspects, the user interface may be configured to prompt the user to assay a calibration sample of the user's blood to obtain a calibration value, if a third condition is met.

In certain aspects, the user interface may be configured to determine the existence of a condition relating the subject.

In certain aspects, the condition may include a determination of whether the subject is asleep In certain aspects, the third condition may be met if the condition does not exist.

In certain embodiments, an analyte measurement system may include an electrochemical sensor generating a signal corresponding to an analyte concentration level in a biofluid of a subject, and a processor unit comprising a user interface for prompting a user to select a time for obtaining a calibration sample of the user's blood to obtain a calibration value; and configured to correlate the calibration value to at least one of the signals from the sensor if the current time corresponds to the selected time.

In certain aspects, the user interface may be configured to prompt the user to select a date and a time for calibration.

In certain aspects, the user interface may be configured to prompt the user to select a time for recurrent daily calibration.

In certain embodiments, an analyte measurement system may include an electrochemical sensor generating a signal corresponding to an analyte concentration level in a biofluid of a subject, a processor configured to determine whether calibration is accepted, and a user interface providing a user the option to obtain a calibration sample of the user's blood to obtain a calibration value if calibration is accepted and wherein the processor is configured to correlate the calibration value to at least one of the signals from the sensor.

In certain aspects, the predetermined time may be fifteen minutes.

In certain aspects, the calibration may be accepted if the rate of change of the signal is within a predetermined threshold.

In certain aspects, the processor may be configured to determine the likelihood of successful calibration.

In certain aspects, the user interface may be configured to provide an icon relating to the likelihood of successful calibration.

In certain embodiments, an analyte measurement system may include an electrochemical sensor generating a signal corresponding to an analyte concentration level in a biofluid of a subject, a processor configured to determine a predetermined calibration time, to determine a prospective calibration window running prior to the predetermined calibration time, and to allow calibration if a reference analyte measurement is available during the prospective calibration window.

In certain aspects, processor may be configured to provide a grace period after the predetermined calibration time, and provide an alarm if no calibration is performed during the time period beginning with the predetermined calibration time and ending with the expiration of the grace period.

In certain aspects, processor may be configured to suppress the alarm if a reference analyte measurement is available during the prospective calibration window.

In certain aspects, the user interface may be configured notify the user if a reference analyte measurement is being accepted for calibration.

In certain aspects, the prospective calibration window may include a time period of 10 minutes prior to the predetermined calibration time.

In certain aspects, the prospective calibration window may include a time period of 30 minutes prior to the predetermined calibration time.

In certain aspects, the prospective calibration window may include a time period of one hour prior to the predetermined calibration time.

In certain embodiments, an analyte measurement system may include an electrochemical sensor generating a signal corresponding to an analyte concentration level in a biofluid of a subject, a processor configured to determine a condition relating to the stability of the sensor signal, and to allow calibration if the sensor stability is within a predetermined threshold.

In certain aspects, the predetermined threshold may include a sensor stability of about 1 mg/dL/min.

In certain aspects, a duration of sensor operation and the stability of the sensor signal at a reference duration of sensor operation may be determined.

In certain aspects, the user interface may request a calibration if the stability of the sensor signal at the reference duration of sensor operation is below a threshold.

In certain aspects, the reference duration of sensor operation may include an elapsed time following insertion of the sensor in the subject.

In certain aspects, the reference duration may include four hours.

In certain aspects, the analyte may be glucose.

In certain aspects, the assayed calibration sample may be obtained from a fingerstick testing site.

In certain aspects, the assayed calibration sample may be obtained from an alternative site test.

In certain aspects, the location may be located along a leg of a user.

In certain aspects, the location may be located along an abdomen of a user.

In certain aspects, obtaining the calibration measurement may include determining the calibration measurement in less than or equal to about 1 μL of blood.

In certain aspects, the calibration value may be compared to at least one signal from the sensor for use in calibrating the sensor.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method, the method comprising:
   positioning a portion of an analyte sensor through a skin surface in fluid contact with biofluid under the skin surface of a subject;
   generating a signal from the analyte sensor, the signal corresponding to an analyte concentration level in the biofluid;
   storing, using one or more processors, a pre-set calibration schedule and at least one user-defined time period having a beginning time set by the subject and an ending time set by the subject;

prompting, using the one or more processors, the subject to assay a calibration sample of the subject's blood to obtain a calibration value only when a first condition is met;

selecting, using the one or more processors, a first time frame and a maximum number of calibrations in the first time frame;

confirming, using the one or more processors, that a time for prompting the subject to assay the calibration sample is outside of the user-defined time period; and correlating, using the one or more processors, the calibration value to at least one of the signals from the sensor when the first condition is met;

wherein the first condition is met when fewer than the maximum number of calibrations have occurred in the first time frame; and prior to prompting the subject to assay the calibration sample, performing a data validation routine including a check for sensor electronics hardware error, a check on the data quality, and a check for current and/or voltage saturation.

2. The method of claim 1, further comprising selecting a second time frame.

3. The method of claim 2, further comprising selecting a maximum number of calibrations in the second time frame.

4. The method of claim 3, wherein the first condition is met when fewer than the maximum number of calibrations have occurred in the second time frame.

5. The method of claim 1, further comprising prompting the subject to assay a calibration sample of the subject's blood to obtain a calibration value, when a second condition is met.

6. The method of claim 5, further comprising prompting the subject to assay a calibration sample of the subject's blood to obtain a calibration value, when a third condition is met.

7. The method of claim 6, further comprising determining a presence of a condition relating to the subject.

8. The method of claim 7, wherein the condition relating to the subject comprises a determination of whether the subject is asleep.

9. The method of claim 7, wherein the third condition is met when the condition relating to the subject does not exist.

10. The method of claim 5, wherein the second condition is met when a waiting period between a previous calibration event associated with the pre-set calibration schedule and the time when the subject was prompted to assay the calibration sample has elapsed.

11. The method of claim 1, wherein the analyte concentration level is a glucose concentration level.

12. The method of claim 1, wherein obtaining the calibration value comprises determining a calibration measurement in less than or equal to about 1 µL of blood.

13. The method of claim 1, wherein the calibration value is compared to at least one of the signals from the sensor to calibrate the sensor.

14. The method of claim 1, further comprising:
confirming that a calibration sample was not obtained within a predetermined period of time after the prompting the subject to assay the calibration sample has elapsed;
confirming that a reference measurement is available during a period of time prior to the prompting the subject to assay the calibration sample; and
suppressing an alarm associated with confirming that the calibration sample was not obtained.

15. The method of claim 1, wherein the pre-set calibration schedule is not alterable by the subject.

16. An apparatus, comprising:
a processing unit; and
a memory coupled to the processing unit, the memory storing instructions which, when executed by the processing unit, causes the processing unit to receive a signal from a sensor in fluid contact with biofluid under a skin surface of a subject, the signal corresponding to an analyte concentration level in a biofluid, store a pre-set calibration schedule and at least one user-defined time period having a beginning time set by the subject and an ending time set by the subject, prompt the subject to assay a calibration sample of the subject's blood to obtain a calibration value, only when a first condition is met, select a first time frame and a maximum number of calibrations in the first time frame, confirm that a time for prompting the subject to assay the calibration sample is outside of the user-defined time period, and correlate the calibration value to at least one of the signals from the sensor when the first condition is met, wherein the first condition is met when fewer than the maximum number of calibrations have occurred in the first time frame, and further, wherein prior to the processing unit prompting the subject to assay the calibration sample, the memory further includes instructions which, when executed by the processing unit, causes the processing unit to perform a data validation routine including a check for sensor electronics hardware error, a check on the data quality, and a check for current and/or voltage saturation.

17. The apparatus of claim 16, wherein the memory further includes instructions which, when executed by the processing unit, causes the processing unit to select a second time frame.

18. The apparatus of claim 17, wherein the memory further includes instructions which, when executed by the processing unit, causes the processing unit to select a maximum number of calibrations in the second time frame.

19. The apparatus of claim 18, wherein the first condition is met when fewer than the maximum number of calibrations have occurred in the second time frame.

20. The apparatus of claim 16, wherein the memory further includes instructions which, when executed by the processing unit, causes the processing unit to prompt the subject to assay a calibration sample of the subject's blood to obtain a calibration value, when a second condition is met.

21. The apparatus of claim 20, wherein the memory further includes instructions which, when executed by the processing unit, causes the processing unit to prompt the subject to assay a calibration sample of the subject's blood to obtain a calibration value, when a third condition is met.

22. The apparatus of claim 21, wherein the memory further includes instructions which, when executed by the processing unit, causes the processing unit to determine a presence of a condition relating to the subject.

23. The apparatus of claim 22, wherein the condition relating to the subject comprises a determination of whether the subject is asleep.

24. The apparatus of claim 22, wherein the third condition is met when the condition relating to the subject does not exist.

25. The apparatus of claim 20, wherein the second condition is met when a waiting period between a previous calibration event associated with the pre-set calibration schedule and the time when the subject was prompted to assay the calibration sample has elapsed.

26. The apparatus of claim 16, wherein the analyte concentration level is a glucose concentration level.

27. The apparatus of claim 16, wherein the instructions to obtain the calibration value include instructions to determine a calibration measurement in less than or equal to about 1 μL of blood.

28. The apparatus of claim 16, wherein the calibration value is compared to at least one of the signals from the sensor to calibrate the sensor.

* * * * *

UNITED STATES PATENT AND TRADEMARK OFFICE
CERTIFICATE OF CORRECTION

PATENT NO. : 10,092,229 B2
APPLICATION NO. : 13/172823
DATED : October 9, 2018
INVENTOR(S) : Marc Barry Taub et al.

Page 1 of 1

It is certified that error appears in the above-identified patent and that said Letters Patent is hereby corrected as shown below:

In the Specification

Column 8, Line 35, replace "and pending U.S." with --and U.S.--.

Signed and Sealed this
Twenty-sixth Day of March, 2019

Andrei Iancu
*Director of the United States Patent and Trademark Office*